US008709496B2

(12) United States Patent
Bayerl

(10) Patent No.: US 8,709,496 B2
(45) Date of Patent: Apr. 29, 2014

(54) USE OF DEUTERIUM OXIDE FOR THE TREATMENT OF VIRUS-BASED DISEASES OF THE RESPIRATORY TRACT

(75) Inventor: Thomas Bayerl, London (GB)

(73) Assignee: D2 Bioscience Group Ltd., Hamilton (BM)

( * ) Notice: Subject to any disclaimer, the term of this patent is extended or adjusted under 35 U.S.C. 154(b) by 0 days.

(21) Appl. No.: 13/478,808

(22) Filed: May 23, 2012

(65) Prior Publication Data

US 2012/0231088 A1 Sep. 13, 2012

Related U.S. Application Data

(63) Continuation of application No. 12/652,939, filed on Jan. 6, 2010, now abandoned.

(51) Int. Cl.
| | | |
|---|---|---|
| A61K 33/00 | (2006.01) | |
| A61P 31/20 | (2006.01) | |
| A61P 11/02 | (2006.01) | |
| A61P 31/14 | (2006.01) | |
| A61P 11/00 | (2006.01) | |
| A61P 31/16 | (2006.01) | |

(52) U.S. Cl.
USPC ........................................................ 424/600

(58) Field of Classification Search
None
See application file for complete search history.

(56) References Cited

U.S. PATENT DOCUMENTS

| | | | |
|---|---|---|---|
| 5,028,431 | A | 7/1991 | Franz et al. |
| 5,223,269 | A | 6/1993 | Liepins et al. |
| 5,233,269 | A | 8/1993 | Lien |
| 5,788,953 | A | 8/1998 | Somlyai |
| 6,009,876 | A | 1/2000 | Yavitz et al. |
| 6,977,164 | B2 | 12/2005 | WalkerPeach et al. |
| 7,132,452 | B2 | 11/2006 | Lee et al. |
| 7,767,215 | B2 | 8/2010 | McClellan et al. |
| 2002/0183380 | A1 | 12/2002 | Hunter et al. |
| 2004/0234450 | A1 | 11/2004 | Howes et al. |
| 2005/0187212 | A1 | 8/2005 | Ohki et al. |
| 2007/0129282 | A1 | 6/2007 | Ahlem et al. |
| 2007/0141074 | A1 | 6/2007 | Schubert |
| 2008/0113035 | A1 | 5/2008 | Hunter et al. |
| 2009/0011022 | A1 | 1/2009 | Bayerl et al. |
| 2009/0131486 | A1 | 5/2009 | Hansen et al. |
| 2009/0156473 | A1 | 6/2009 | Schubert |
| 2010/0329994 | A1 | 12/2010 | Bayerl et al. |
| 2011/0076331 | A1 | 3/2011 | Bayerl et al. |

FOREIGN PATENT DOCUMENTS

| | | |
|---|---|---|
| DE | 3019434 | 1/1982 |
| DE | 4427690 | 2/1996 |
| DE | 10 2006 026 464 | 12/2007 |
| DE | 10 2007 031 397 | 1/2009 |
| EP | 0893123 | 1/1999 |
| EP | 1 092 433 | 4/2001 |
| EP | 2110132 | 10/2009 |
| WO | 96/03996 | 2/1996 |
| WO | 99/62510 | 9/1999 |
| WO | 2005/016234 | 2/2005 |
| WO | 2005/063281 | 7/2005 |
| WO | 2006/022460 | 3/2006 |
| WO | 2007/129962 | 11/2007 |
| WO | 2008/046407 | 4/2008 |

OTHER PUBLICATIONS

Carp et al. (Influence of Heavy Water (D2O) on the Multiplication of Adeno and Mengo Virus, Experientia 23/9, 1967, pp. 786-787).*
Chapter 171: „Gram-positive cocci (Pneumococcal infections) In: Beers et al.: „The Merck Manual, 18th Edition 2006, Merck research laboratories, USA, XP002574619, Seiten 1-2991.
http://en.wikipedia.org/wiki/Norwegian_heavL.water_sabotage.
No date of publication. "Norwegian Heavy Water Sabotage", Publisher: Wikipedia; No Edition or volume; Whole Web page is pertinent. No Author Provided.
White et al., „Effect of Colchicine, vinblastine, D2O and cytochalasin B on elastase secretion, protein synthesis and fine structure of mouse alveolar macrophages, Journal of the Reticuloendothelial Society Apr. 1981, Bd. 29, Nr. 4, Apr. 1981, S. 295-304.
Nancy Oleinick, http://www.photobiology.info/Oleinick.html, 2005, Publisher: Photobiologial Sciences Online, no location given; No edition; No volume; Whole Web Page is Pertinent.
Stein ("Catalysis by Human Leukocyte Elastase: Substrate Structural Dependence of Rate-Limiting Protolytic Catalysis and Operation of the Charge Relay System," J . Am. Chem. SOC1. 983, 105,51 11-51 16).
Giudice et ai, "Cloning and Primary Structural Analysis of the Bullous Pemphigoid Autoantigen BP180," Journal of Investigative Dermatology (1992) 99, 243-250).
Liu et al., "A critical role for neutrophil elastase in experimental bullous pemphigoid," J Clin Invest. 2000; 105 (1 ):113-123.
http://en.wikipedia.org/wiki/HeavL.water; No author; No date of Publication; "Heavy Water", Publisher: Wikipedia, no location given; No edition; No volume; Whole Web Page is Pertinent.
http://www.sircuitskin.com/inc/sdetail/11707; Author is Sircuit Cosmeceuticals®; No Title; Publisher: Sircuit Cosmeceuticals®; No location given; No edition, No volume; Whole Web Page is Pertinent.
Email Containing Google Search Results, From James H. Jenkins (ASRC) USPTO, dated Aug. 25, 2011; no publisher, no edition, no volume, whole attached web page is pertinent (pp. 1-2, p. 1 pertinent).
Ravariu, et al. (2004) "A silicon Nanoporous Membrane Used for Drug Delivery", Semiconductor Conference, CAS 2004 Proceedings, 2004 International, pp. 101-104 (IEEE) No edition; no volume, p. 101 pertinent.
Neyts, et al. (1999) Antimicrobial Agents and Chemotherapy, 43(12): 2885-92.
Lindwall, et al. (Feb. 9, 2006) Journal of Investigative Dermatology, 126(4): 841-48.
Wainwright (2003) International Journal of Antimicrobial Agents, 21 (6): 510-20.

(Continued)

*Primary Examiner* — San-Ming Hui
*Assistant Examiner* — Kathrien Cruz
(74) *Attorney, Agent, or Firm* — McDonnell Boehnen Hulbert & Berghoff LLP

(57) ABSTRACT

The present invention relates to the use of deuterium oxide for the prophylaxis and/or therapy of virus-based diseases of the respiratory tract.

21 Claims, 12 Drawing Sheets

(56) References Cited

OTHER PUBLICATIONS

Muller-Breitkreutz, et al. (1995) Journal of Photochemistry and Photobiology, 30: 63-70.

Kuschner et al. „Pharmacological uses and perspectives of heavy water and deuterated compounds, Canadian Journal of Physiology and Pharmacology, Ottawa, Ont. CA, Bd. 77, Nr. 2, Feb. 1, 1999, S. 79-88.

Bastow T J et al: "H and C NMR studies of water and heavy water absorption in poly(vinyl alcohol) hydrogels", Journal of Membrane Science, Elsevier Scientific Publ. Company. Amsterdam, NL, Bd. 131, Nr. 1-2, Aug. 6, 1997, Seiten 207-215.

Carp et al., "Influence of heavy water (D2O) on the multiplication of adeno and mengo virus", Experientia (1967), vol. 23, pp. 786-787.

Takeda et al., "Mechanisms of cytotoxic effects of heavy water (deuterium oxide: D20) on cancer cells", Anticancer Drugs (1998), vol. 9(6), pp. 715-725.

Lifson, "(D2 180 (deuterium oxide) method for CO2 output in small mammals and economic feasibility in man", Journal of Applied Physiology (1975), vol. 39 (4). Abstract only.

Pauwels "Global strategy for the diagnosis, management and prevention of chronic obstructive Pulmonary Disease", American Journal of Respiratory and Critical Care Medicine (2001), vol. 163, pp. 1256-1276.

Marjolaine Vareille, et al., (2011) Clin. Microbiol. Rev., "The Airway Epithelium: Soldier in the Fight against Respiratory Viruses", vol. 24(1): pp. 210-229.

Mark D. Wareing, et al. (2007), Viral Immunology, "CXCR2 Is required for Neutrophil Recruitment to the Lung during influenza Virus Infection, But is not Essential for Viral Clearance", vol. 20(3), pp. 369-378.

* cited by examiner

Figure 7

Table 1:

Infection of a culture of the cell line A549 with various viruses

| Virus type / Virus strain | Number in treated group | Number in control group |
|---|---|---|
| Rhinoviruses / RV-16 | 7 ± 2 | 16 ± 3 |
| HSV-1 / McIntyre | 4 ± 1 | 11 ± 2 |
| Varicella Zoster / Ellen | 3 ± 1 | 6 ± 1 |
| Coronavirus / HCoV 229E | 6 ± 2 | 15 ± 3 |
| Influenza A / H1N1 | 4 ± 1 | 9 ± 1 |
| Influenza B / Hongkong | 3 ± 2 | 10 ± 2 |
| HPIV-1 / Washington | 7 ± 2 | 11 ± 2 |
| HRSV / Long | 2 ± 1 | 8 ± 1 |
| HMPV A1 | 4 ± 1 | 9 ± 1 |
| Human adenoviruses 3 / GZ1 | 6 ± 1 | 9 ± 2 |
| Hum. enteroviruses 71 / SHZH98 | 3 ± 2 | 8 ± 2 |

Figure 8

Table 2

Infection of a culture of the cell line A549 with various viruses

| Virus /Strain | Viral count Treated group | Viral count Control group |
|---|---|---|
| Rhinovirus /RV-16 | 2 ± 1 | 5 ± 1 |
| Herpes HSV-2 / 764 | 1 ± 1 | 4 ± 1 |

Figure 9

Table 3

$D_2O$ efficacy for the therapy of Aphthosis herpetica

| Indicator | Treated $D_2O$ | Control $H_2O$ |
|---|---|---|
| Number of aphthae treated | 17 | 20 |
| Mean total symptom score | 3.2 ± 0.4 | 6.8 ± 0.6 |
| Mean max. size of aphtha (mm) | 2.1 ± 0.3 | 3.9 ± 0.4 |
| Mean period until complete external healing (days) | 1.8 ± 0.6 | 3.5 ± 0.8 |
| Mean period until pain-free (days) | 1.2 ± 0.3 | 3.0 ± 0.5 |
| Mean time between first symptom and gel application (hours) | 1.5 ± 0.5 | 1.6 ± 0.7 |

Figure 10

Table 4

D$_2$O efficacy for the prophylaxis of a rhinovirus infection, HRV-39 infection

| Indicator<br>6 hours before infection | Treated<br>D$_2$O | Control<br>H$_2$O |
|---|---|---|
| Number of assessable test persons | 10 | 9 |
| Mean total symptom score (<TSS>) | 1.2 ± 0.15 | 2.2 ± 0.4 |
| Mean concentration HRV-39 RNA / ml | 3.2 ± 0.5 | 4.0 ± 0.8 |

Figure 11

Table 5

D$_2$O efficacy for the prophylaxis of a rhinovirus infection, HRV-39 infection

| Indicator<br><br>2 hours after infection | Treated<br>D$_2$O | Control<br>H$_2$O |
|---|---|---|
| Number of assessable test persons | 7 | 6 |
| Mean total symptom score (<TSS>) | 1.4 ± 0.2 | 2.3 ± 0.3 |
| Mean concentration HRV-39 RNA / ml | 3.5 ± 0.4 | 4.5 ± 0.6 |

Figure 12

Table 6

D$_2$O efficacy for the therapy of acute bronchitis after infection by the human respiratory syncytial virus (HRSC)

| Indicator | Treated D$_2$O | Control H$_2$O |
|---|---|---|
| Number of assessable test persons | 7 | 5 |
| Mean normalized HRSV RNA conc. | 2.3 ± 0.4 | 4.4 ± 0.8 |
| Mean FEV1 / FVC (%) | 76 ± 5 | 63 ± 9 |

USE OF DEUTERIUM OXIDE FOR THE TREATMENT OF VIRUS-BASED DISEASES OF THE RESPIRATORY TRACT

RELATED APPLICATIONS

This application is a continuation of U.S. application Ser. No. 12/652,939 filed Jan. 6, 2010, which claims the benefits of German Patent Application No. 102009003942.2 filed Jan. 7, 2009, which are incorporated herein by reference in their entirety.

FIELD OF THE INVENTION

The present invention relates to the use of deuterium oxide ($D_2O$) for the prophylaxis and/or therapy of virus-based diseases of the respiratory tract.

BACKGROUND

Diseases caused by viruses (virus infections) occur throughout the world and represent a serious problem in medicine, in particular because of the high variability, adaptability and mutation rate of viruses. Viruses are small particles of ca. 15 to 400 nm diameter, which are not capable of replicating themselves alone, but require a host cell for this. On the basis of their host specificity, a distinction is made between viruses which infect animals (invertebrates and vertebrates), plants, bacteria or algae, fungi and protozoa. Viral infections in general are characterized by a high reproduction rate of the viral particles in the affected host cells, which can be described by an exponential or power law. The reproductive cycle of viruses takes place via the injection of their nucleic acid (viral RNA or viral DNA) into the host cell, in which the replication of the nucleic acid takes place by utilization of the replication apparatus of the host cell. Here a distinction is made between the lytic and the lysogenic cycle. In the lytic cycle (active infection), after the injection of the nucleic acid the replication of the viral nucleic acid takes place in the cell nucleus of the host cell, and assembly of the new viral particles in the cytoplasm, after which the host cell is finally lysed (destroyed) and the viruses are released. The viruses thus released infect further host cells. In the lysogenic cycle, the nucleic acid of the virus is integrated into the genome of the host cell, where it at first remains without destroying the host cell. Due to external influences (e.g. UV radiation, addition of mutagenic substances) this lysogenic cycle can change into an aforesaid lytic cycle. In the case of RNA viruses, after infection therewith a transcription of the RNA into DNA is necessary so that replication via the host cell can take place. This process takes place via reverse transcriptase, an enzyme which is encoded by viral genes and must first be synthesized in the host cell in order to transcribe the viral RNA into viral DNA which is then in turn replicated by the DNA polymerase of the host cell.

Viruses are capable of infecting a broad spectrum of cells, organs and hosts. Each viral species specifically infects preferred cells, such as for example cells of the stomach, intestine, the skin and the respiratory tract. This leads to many so-called virus-based diseases.

Among these, virus-based diseases of the respiratory tract are a widespread and major pathological problem in medicine, in particular in man. At a percentage level of 90%, infection by viruses is the commonest cause of respiratory diseases that are caused by pathogens such as viruses and bacteria. Viruses which cause such virus-based diseases of the respiratory tract include in particular influenza viruses, parainfluenza viruses, respiratory syncytial viruses, coronaviruses, rhinoviruses, Coxsackieviruses, echoviruses, herpes viruses, human metapneumoviruses and adenoviruses, but are not limited to these.

In general, the organs affected are primarily the nose, nasal sinuses, oral cavity, tonsils, pharynx, trachea, bronchi and lung. Depending on the virus type and the severity of the infection, the viruses can affect limited areas of the respiratory tract locally or else spread to several areas. Secondarily, the ear, in particular the middle ear and the Eustachian tubes, can be affected by the viral infection.

As a rule, the viruses first infect epithelial cells, such as for example dermal, mucous and mucous membrane cells of the upper and/or lower respiratory tract, such as for example epithelial cells in the mouth, nose and pharynx and epithelial cells of the bronchioli, alveoli and trachea of the lung, followed by intense reproduction of the virus in the host cell and death of the infected host cell. The host reacts with an immune response which leads to various symptomatic syndromes. For example, the spreading of rhino-viruses takes place mainly in the epithelial cells of the mouth and nose and causes a local infection there by cold or flu symptoms such as rhinitis (head cold).

Virus-based diseases of the respiratory tract also include for example acute or chronic rhinitis, (acute or chronic nasal mucous membrane inflammation), pharyngitis, herpangina, angina lateralis, tonsillitis, laryngitis, tracheitis, acute bronchiolitis, acute bronchitis, aveolitis and pneumonia. Other diseases, such as for example acute or chronic sinusitis (acute or chronic nasal sinus inflammation), gingiovastomatitis herpetica (also known as stomatitis aphthosa, somatis herpetica) (inflammation of the oral mucous membrane and the gums), aphtosis herpetica, herpes nasalis, acute asthma, COPD (chronic obstructive pulmonary disease) and laryngeal diphtheria, which according to the invention are also among the virus-based diseases of the respiratory tract, can be triggered or intensified. The simultaneous onset e.g. of rhinitis and sinusitis (called rhinosinusitis) or of laryngitis, tracheitis and bronchitis (called laryngo-tracheo-bronchitis), or consecutive onset (successive onset) of several of these aforesaid diseases is common. Secondary diseases of the respiratory tract include for example middle ear inflammation (otitis media) and/or inflammation of the Eustachian tubes, which according to the invention are also virus-based diseases of the respiratory tract.

The symptoms and thus the syndrome which is caused by viral infections of the respiratory tract are very similar for most viruses. Nonetheless some diseases are caused preferentially by a specific viral type (see below). Further, the symptoms of the infection depend on the severity of the infection and the immune defenses of the host. By way of example, some such specific viruses, their infection route and pathological manifestation are explained in more detail below.

Infection Due to Rhinoviruses

Rhinoviruses are small, envelope-free RNA viruses of the Picornavirus group, which infect the upper and lower areas of the respiratory tract of the host, in particular of a mammal such as for example man (human pathogenic rhinoviruses or human rhinoviruses, 117 serotypes known), cattle (bovine rhinoviruses), monkeys and ferrets.

The replication of the human rhinoviruses takes place in the epithelial cells of the upper region of the respiratory tract, particularly in the epithelial cells of the pharynx, mouth and nose, wherein they bind to a cell receptor, the ICAM-1 receptor or the LDL receptor, inject their RNA into the host cell and then reproduce via the lytic cycle. The strongly site-specific replication of the virus is connected with its sensitivity to low pH values such as for example occur in the gastrointestinal tract, and high temperatures (temperature optimum: 32° C.-33° C.). In regions which lie further in the interior of the body, e.g. the lung, the virus is only rarely, and slowly, replicated on account of the physiological temperature of 37° C. prevailing there.

The diseases caused by human rhinoviruses mainly include diseases of the upper respiratory tract, in particular rhinitis and pharyngitis, and acute bronchitis. These diseases often lead to secondary infections, e.g. sinusitis (nasal sinus inflammation) and otitis media (infection of the middle ear). Less commonly, diseases of the lower respiratory tract such as for example acute asthma and COPD are triggered by rhinovirus infections. Rhinoviruses are the cause of ca. 40%-50% of all colds and flu and of ca. 34% of all respiratory infectious diseases.

Infection Due to Influenza Viruses

Influenza virus are membrane-coated RNA viruses and belong to the Orthomyxidae group. They infect both mammals, in particular man, dogs, horses, pigs and the like, and birds. The strains influenza A and influenza B are pathogenic in humans. Transmission occurs via droplets and/or direct contact.

The replication of the viruses takes place in the epithelial cells of the upper and lower respiratory tract, but particularly in the epithelial cells of the upper and lower trachea, the bronchi and the aveoli of the lung. Their reproduction takes place by the lytic cycle.

Influenza viruses lead to the pathological manifestation of what is generally termed flu. Mild infections induce colds and flu, such as rhinitis and pharyngitis, accompanied by cough, shivering, headaches, weakness and fever. Severe influenza infections affect the upper and also the lower regions of the respiratory tract and trigger diseases such as for example pharyngitis, tracheobronchitis, acute bronchitis, bronchiolitis and also less commonly and in particularly severe cases pneumonia. Infections with influenza A can even take a fatal course.

Infection Due to Parainfluenza Viruses

Parainfluenza viruses are membrane-coated RNA viruses of medium size, belong to the Paramyxoviridae group and can be transmitted via droplets and/or direct contact. They infect mammals in particular, such as man. Strains pathological to humans, which affect (infect) the respiratory system in man, in particular small children, children, immunosuppressed and elderly people, are the human parainfluenza virus 1, human parainfluenza virus 2 and human parainfluenza virus 3. They are also called respiroviruses.

Parainfluenza viruses reproduce optimally at physiological pH (pH 7.4-pH 8) and temperatures of up to 37° C. They infect epithelial cells of the upper and lower respiratory tract and reproduce via the lytic cycle.

In man, parainfluenza virus 1, parainfluenza virus 2 and parainfluenza virus 3 cause mild infections with cold and flu symptoms which resemble those of rhinitis, pharyngitis and acute bronchitis, and also severe infections, in particular laryngo-tracheo-bronchitis, tracheo-bronchitis, bronchiolitis and pneumonia. They are the main cause of laryngitis subglottica.

Infections Due to Respiratory Syncytial Virus (RSV)

The respiratory syncytial virus (RSV) is a membrane-coated RNA virus which is transmitted via droplets and/or direct infection. Both strains pathogenic in man and strains pathogenic in animals are known.

The replication of the RSV takes place firstly in the nasopharynx, during which the RSV binds to glycosaminoglycans of surface epithelial cells and injects its RNA into the host cell. In severe infections, the viruses can penetrate into the lower part of the respiratory tract and reproduce there, particularly in the epithelial cells of the bronchioli and aveoli, via the lytic cycle.

An infection due to RSV firstly causes symptoms which resemble those of rhinitis and pharyingitis in the upper respiratory tract, accompanied by slight fever and cough. Infection of the lower respiratory tract is common and it gives rise to pathogenic manifestations such as for example tracheitis, bronchitis and bronchiolitis. Less common pathogenic manifestations are pneumonia, laryngeal diphtheria and, as a secondary disease, middle ear inflammation.

Infections Due to Herpes Viruses

Herpes viruses are widespread in vertebrates, particularly in mammals, and above all in man, horses, pigs, cattle, goats, sheep, cats and dogs. Herpes viruses pathogenic in man (HHV) are classified into alpha, beta and gamma herpes viruses (HHV-1 to HHV-8), with viruses which can infect animals such as for example horses (equine herpes virus), cattle (bovine herpes virus), pigs (porcine herpes virus), cats (feline herpes virus), dogs (canine herpes virus) and chickens (chicken herpes virus 1) belonging to the alpha and gamma viruses.

Among the herpes viruses pathogenic in man, i.e. affecting people, the alpha herpes viruses in particular are of major importance. Herpes simplex virus 1 (HSV-1), herpes simplex virus 2 (HSV-2) and varicella zoster virus (VZV) are numbered among the alpha herpes viruses.

Human alpha herpes viruses as a rule firstly replicate in epithelial cells in the oral and nasal region. Further, the viruses released infect certain nerve cells (neurons) by binding to receptors of the nerve ends in the mouth, which lead to the ganglia of the facial nerve (trigeminus). The viral DNA penetrates into an axon, and is transported into the cytoplasm of the nerve cells and finally into the cell nucleus thereof. There the incorporation of the viral DNA into the genome of the nerve cell takes place and leads to a resting state (latency) in which only a few viral genes are expressed (lysogenic cycle). Various external stimuli can lead to renewed activation of the virus, the final result whereof is the destruction (lysis) of the nerve cell. The viral progeny arising during an activation are firstly transported through the axon to the site or into the region of the original infection and there once again infect epithelial cells.

HSV-1 can cause diseases of the respiratory tract, in particular in the region of the mouth. These for example include herpes nasalis, aphtosis herpetica and gigiovastitis herpetica. Furthermore, HSV infections can also lead to pneumonia.

Infections Due to Coronaviruses

Coronaviruses are membrane-coated RNA viruses which infect vertebrates, in particular mammals such as man, dogs, cats, cattle, pigs and some rodents, and birds. Coronaviruses are transmitted by droplet infection.

Among the strains pathogenic in man, human coronavirus (HCo) 229E, HCo-OC43, HCoV-NL63 and SARS infect the epithelial cells of the respiratory tract in man, in particular the upper respiratory tract. Reproduction takes place via the lytic cycle.

The diseases caused by human coronaviruses include rhinitis and pharyngitis. In addition, acute bronchitis, bronchiolitis, pneumonia, SARS (severe respiratory syndrome) and laryngeal diphtheria can be triggered. However, these diseases occur more rarely.

Infections due to human coronaviruses HCo-229E and HCo-OC43 are the cause of ca. one third of all colds and flu in man.

Infection Due to Adenoviruses

Adenoviruses are DNA viruses which infect both animals and man. Of a total of 19 species, 6 adenoviruses pathogenic in man are known (human adenoviruses A to F).

Adenoviruses are characterized by high pH and temperature stability. As a rule they enter the body via the respiratory tract. The reproduction of the adenoviruses is not restricted in location to one region. They can infect epithelial cells of the pharynx, the gastrointestinal tract and the conjunctiva. They reproduce via the lytic cycle.

An infection with adenoviruses leads to cold and flu symptoms which resemble those of rhinitis, pharyngitis, acute bronchitis and/or bronchiolitis.

Infection Due to Enteroviruses

Infections of the respiratory tract can also occur because of enteroviruses such as for example Coxsackie virus 1, Coxsackie virus 2 and echoviruses. Enteroviruses are very acid-stable RNA viruses, which are mainly transmitted fecal-orally and more rarely via droplet infections.

The reproduction of the enteroviruses as a rule begins via an infection of the cells of the small intestine tonsils. From there, the viruses migrate out to the target organs, e.g. the nose, via the bloodstream and lymph. Less commonly, enteroviruses first infect epithelial cells of the mucous membranes of the respiratory tract and reach the intestine from there. The reproduction takes place via the lytic cycle.

Enteroviruses can trigger non-specific, mild infections of the respiratory tract and pharyngo-tonsilitis, bronchiolitis, pneumonia, herpangina, hemorrhagic conjunctivitis and otitis media. Further, infections with enteroviruses cause a large number of further systemic diseases such as for example foot and mouth disease.

Most virus-based diseases of the respiratory tract can at present only be treated symptomatically. Here there are various active substances, for example alpha sympathomimetic agents, anticholinergics, antihistamines, immunosuppressants, and secretolytic agents. Through the administration of such substances, the symptoms, e.g. swellings of the mucous membranes, can be eased. Here the nature and duration of the treatment depends on the pathological manifestation and the severity of the disease. Some of these active substances and their mechanism of action are explained below; however, the enumeration should be understood to be by way of example and not exclusive:

Alpha sympathomimetic agents are alpha adrenergic antagonists which bind to alpha adrenoreceptors in the mucous membranes of the respiratory tract and thus have a stimulant effect on the sympathetic system. Through the stimulation or excitation of the sympathetic system, the vessels of the mucous membranes are narrowed. For this reason, alpha sympathomimetic agents are used for decreasing swelling of the nasal mucous membranes in colds and flu in general, and in particular for the treatment of rhinitis and sinusitis. They are administered topically in the form of nasal sprays or nasal drops. Examples of active substances are naphazoline, tetrazoline, xylometazoline, oxymetazoline and phenylephrine.

Antihistamines primarily have an anti-inflammatory action, in that they inhibit or block histamine receptors in the cells of the skin and mucous membranes of the respiratory tract, whereby the secretion of the inflammation mediator histamine is suppressed. Since the secretion of histamine mainly has a pathological role in allergic reactions, antihistamines are in particular used for the treatment of allergies. However, some antihistamines, which are called first generation H1 antihistamines, also bind to muscarinic receptors in said mucous membranes, resulting in excitation of the sympathetic system, similarly to the sympathomimetic agent. Inter alia, this secondary effect leads to a decrease in the swelling of the mucous membranes and to suppression of bronchial secretion. Antihistamines can be administered both topically and orally. Examples are diphenhydramine, tripolidine and chlorpheniramine.

Immunosuppressants are pharmaceuticals which suppress the immune response of the host and thus have an inflammation-inhibiting action. They include for example gluco-corticoids, cytostatics and (chimeric) antibodies.

Secretolytic agents are substances, such as for example salt water, camomile and sage, which are administered topically and result in the outflow of for example blocked nasal secretions in rhinitis and sinusitis.

All the treatment approaches described above are exclusively based on a therapy of the symptoms and hence the consequences of a viral infection of the respiratory tract. None of these treatment approaches is based on a prophylactic or therapeutic action which already sets in during the viral infection or the direct consequences of an infection with a virus, and limits or blocks, preferably prevents, the outbreak of the disease, i.e. an antiviral action. In the sense of this invention, "antiviral action" should be understood in general as blocking or inhibition of the infection, replication and/or reproduction of a virus. "Replication" in the sense of the invention should be understood to mean the multiplication of the nucleic acid, both DNA and also RNA, of a virus. "Reproduction", "reproduction of the virus" or "viral reproduction" should also be understood to mean the replication as defined above, and furthermore all processes which lead to an intact virus, such as the processing of a synthesized long viral protein into small protein segments and the assembly of the viral particles, such as for example the nucleocapsids.

Furthermore, for the said treatment approaches considerable side-effects are reported in the literature, such as for example rhinitis medicamentosus with treatment with alpha sympathomimetic agents, dermal atrophy with treatment with glucocorticoids, Cushing syndrome and adrenal cortex atrophy with long-term, systemic administration of glucocorticoids and severe exhaustion with histamine treatment.

Hence one important approach for the prophylaxis and/or therapy of virus-based diseases of the respiratory tract is the development of antiviral active substances. The aim is to intervene in the infection, replication and/or reproductive cycle of a virus, for example by inhibiting or blocking the viral infection of a host cell, the replication of the viral nucleic acid, the expression of the viral proteins encoded by the viral nucleic acid, the reproduction of the virus in the host cell and/or the release of the virus from the host cell, e.g. by budding.

However, at present a treatment of virus-based diseases of the respiratory tract with antiviral active substances is only known for infection by some viruses. Furthermore, these active substances have considerable disadvantages in that they cause undesired side-effects. Different mechanisms of action of such antiviral active substances, also called virustatics or virostatics, are described in more detail below.

For the treatment of infections due to influenza virus A and influenza virus B, neuramidase inhibitors such as zanamivir (Relenza®) and oseltamivir (Tamiflu®) are known. The enzyme neuramidase inhibited by these active substances helps newly formed viruses to bud off from the host cell. After the budding, they can then infect further host cells. Through the inhibition of the neuramidase, infection of further host cells should be avoided (Snell N J C, *New treatments for viral respiratory tract infections—opportunities and problems*, Journal of Antimicrobial Chemotherapy, 2001, Vol. 47, 251-259; Sugrue R I et al., *Antiviral drugs for the Control of Pandemic Influenza Virus*, Annals Academy of Medicine, 2008, Vol. 37, 518-524).

Further, for the treatment of infections due to influenza virus A, M2 channel blockers (amantadine, rimantadine) are known. These prevent the "uncoating", i.e. the release of the viral nucleocapsids into the cytoplasm of the host cell (Snell N J C, *New treatments for viral respiratory tract infections—opportunities and problems*, Journal of Antimicrobial Chemotherapy, 2001, Vol. 47, 251-259; Sugrue R I et al., *Antiviral drugs for the Control of Pandemic Influenza Virus*, Annals Academy of Medicine, 2008, Vol. 37, 518-524).

For the treatment of infections due to rhinoviruses or enteroviruses, the administration of intranasal interferon and of immune serum globulin is known (Rotbart A, Hayden F G, *Picornavirus Infections A primer for the practitioner*, Arch Fam Med. 2000, Vol. 9, 913-920).

Furthermore, virostatic agents have been developed which block or inhibit enzymes such as for example DNA polymerase, reverse transcriptase or proteases and thus block or inhibit the replication of the virus or the processing of a synthesized long viral protein into small protein segments. Examples of such therapeutic approaches are found in particular in the therapy of HIV infections. However virostatic agents which are administered systemically or topically are also known in the field of the therapy of virus-based diseases of the respiratory tract. Examples of these are the active substances ribavirin (Flumadin®), aciclovir, valaciclovir, foscarnet and peniclovir.

For the treatment of infections due to respiratory syncytial viruses (RSV) or enteroviruses and severe bronchiopulmonary diseases triggered thereby, the inhalation of ribavirin (Flumadin®) is known (Snell N J C, *New treatments for viral respiratory tract infections—opportunities and problems*, Journal of Antimicrobial Chemotherapy, 2001, Vol. 47, 251-259). Ribavirin is a nucleoside analog which is integrated into the RNA of the virus and thus blocks the RNA polymerase. This results in chain termination and hence the stoppage of RNA replication and viral reproduction.

For the treatment of infections due to herpes viruses such as HSV-1, HSV-2 and VZV, orally or topically administered virostatic agents such as aciclovir, valaciclovir, foscarnet and penciclovir can be used.

For the administration of the virostatic agents described for the treatment of virus-based diseases of the respiratory tract, two approaches are known:
- systemic administration: through systemic administration of virostatic agents, a significant decrease in the activation of viruses present in host cells can be achieved, since the active substances block or inhibit the reproduction of the viral nucleic acid in the cell nucleus or the assembly of the viral particles into complete viruses in the cytoplasm of the host cells;
- topical administration: through topical administration of virostatic agents, for example via a nasal spray (aerosol) or nasal drops, in the region of the respiratory tract, e.g. the nose, for a first infection by the virus, the further path of the reproduction of the viruses can be prevented at an early stage, which can lead to a faster decrease in the swelling of the mucous membranes.

However, both approaches for the administration of such virostatic agents have serious disadvantages:
- with systemic administration, the dose necessary for an effective treatment is relatively high and associated with severe side-effects for the organism treated, such as for example nonspecific immune responses and autoimmune reactions. In the case of aciclovir, many such side-effects are known from the literature. Hence neither long-term nor repeated therapies are advisable nor should they be asked of a patient;
- with topical administration, the quantity of active substance (virostatic agent) which can be released and become bioavailable in the region of the viral infection per unit time is very small. This low bioavailability of the virostatic agent is a considerable obstacle to an effective topical therapy. In the case of the only poorly water-soluble aciclovir, for example, the low bioavailability is due to the poor percutaneous transportation of the active substance. Various chemical modifications of virostatic agents in the context of prodrug designs for improved virostatic agent active substance input have also not led to any improvement in this phenomenon.

Further serious disadvantages are that the antiviral options described for the therapy of virus-based diseases of the respiratory tract can lead to further considerable side-effects and can, as for example in the case of M2 channel blockers, lead to resistant viral strains which excludes treatment of diseases of this kind with such active substances and possible even further active substances for the future.

Moreover, known virostatic agents are very specific and only effective for one or a few viral species. Since however in most infections of the respiratory tract no symptomatic distinction is possible which allows a distinction to be made between the infecting viruses, a successful therapy of a virus-based disease of the respiratory tract cannot be guaranteed for many viruses on account of this high specificity of the known virostatic agents.

The only alternatives to known antiviral active substances for the prophylaxis and/or therapy of virus-based diseases of the respiratory tract which overcome the disadvantages known in the state of the art are vaccinations against the relevant viruses. However, vaccinations against viruses which infect the respiratory tract are in the present state of the art only possible for the influenza viruses (A and B) and RSV (Snell N J C, *New treatments for viral respiratory tract infections—opportunities and problems*, Journal of Antimicrobial Chemotherapy, 2001, Vol. 47, 251-259). Since moreover the viruses are subject to constant mutations, vaccines must always be newly developed. Hence therapies of virally caused diseases cannot be replaced by vaccinations.

There are no other alternatives to the antiviral active substances or virostatic agents disclosed in the state of the art for the prophylaxis and/or therapy of virus-based diseases of the respiratory tract which overcome the disadvantages known in the state of the art.

There is therefore a need to develop improved and more tolerable antiviral active substances which intervene in the replication and/or reproductive cycle of the virus and which preferably already block or inhibit the viral infection of the host cell.

In addition, there is a need to identify antiviral active substances which inhibit the infection, replication and/or reproduction of different viral strains or viral species simultaneously. This is particularly important since with most diseases of the respiratory tract no symptomatic distinction can be made between the various viral strains or viral species which have triggered the infection.

DETAILED DESCRIPTION OF THE INVENTION

The purpose of the invention is therefore to provide improved antiviral active substances for the prophylaxis and/or therapy of virus-based diseases of the respiratory tract.

This purpose is achieved by the present invention. The invention relates in its first subject to the use of deuterium oxide for the prophylaxis and/or therapy of virus-based diseases of the respiratory tract and in its second subject to the use of deuterium oxide for the production of a drug for the prophylaxis and/or therapy of virus-based diseases of the respiratory tract.

A preferred embodiment of the invention relates to the use of deuterium oxide for the prophylaxis and/or therapy of virus-based diseases of the respiratory tract, wherein the virus-based diseases of the respiratory tract are acute rhinitis, chronic rhinitis, rhinitis sicca, pharyngitis, herpangina, angina lateralis, tonsillitis, laryngitis, tracheitis, acute bronchiolitis, chronic bronchiolitis, acute bronchitis, chronic bronchitis, aveolitis, pneumonia, acute sinusitis, chronic sinusitis, gingivostomatitis herpetica, aphtosis herpetica, herpes nasalis, adenovirus pharyngoconjunctitivis, Pfeiffer glandular fever (infectious mononucleosis), acute asthma, chronic asthma, COPD (chronic obstructive pulmonary disease), laryngeal diphtheria, otitis media and/or inflammation of the Eustachian tubes.

Various diseases of the respiratory tract can also arise in parallel or successively. Hence a preferred embodiment of the present invention relates to the use of deuterium oxide for the prophylaxis and/or therapy of virus-based diseases of the respiratory tract wherein there is a combination of two or more virus-based diseases of the respiratory tract. Preferably, these two or more virus-based diseases of the respiratory tract occur simultaneously or successively, in particular as a consequence of the first or of one of the preceding disease(s). In a particularly preferred embodiment, such a combination of two or more virus-based diseases of the respiratory tract relates to rhinosinusitis, tracheo-bronchitis, tracheobronchiolitis, bronchopneumonia, pharyngo-tonsilitis and/or laryngotracheobronchitis. Such a combination according to the invention can in particular consist in the onset of rhinitis sicca, followed by the onset of acute rhinitis (rhinitis acuta). A further example is the onset of acute rhinitis, followed by the onset of chronic rhinitis.

In the sense of the invention, "virus-based diseases of the respiratory tract" should be understood to mean diseases of the respiratory tract which are caused by a virus through a viral infection. The present invention discloses not only the therapy but also the prophylaxis of virus-based diseases of the respiratory tract as defined above. Hence virus-based diseases of the respiratory tract according to the invention should also be understood to mean those diseases of the respiratory tract which should be assigned for a prophylactic treatment of virus-based diseases of the respiratory tract in the sense of the invention. These for example also include diseases typically preceding a virus-based disease of the respiratory tract. This includes in particular rhinitis sicca and indications derived therefrom, such as for example rhinitis sicca anterior, which according to the invention are therefore expressly designated as virus-based disease of the respiratory tract. A preferred use of $D_2O$ according to the invention thus relates to the administration of $D_2O$ with the onset of rhinitis sicca. Under the generally used term "rhinitis", the disclosure in the present invention includes all forms of rhinitis as virus-based diseases of the respiratory tract.

In the sense of the invention, "respiratory tract", also termed airway or respiratory apparatus, should be understood to mean the whole system with all organs responsible for breathing, which are referred to below as "organs to be treated" or "organs of the respiratory tract to be treated". These organs include both the air-conveying organs and also the organs used for gas exchange. The respiratory tract in particular includes nose, nasal sinuses, mouth, pharynx, larynx, windpipe, tonsils, tracheae, main bronchus (bronchus principalis), bronchi, bronchioles, alveoli (pulmonary vesicles) and the lung and the mucous membranes of the respiratory tract, such as the nasal mucous membrane, oral mucous membrane and pharyngeal mucous membrane. A further division of the respiratory tract can be made into the upper respiratory tract or upper part of the respiratory tract, in particular comprising nose, nasal sinuses, mouth, pharynx and tonsils, and the lower respiratory tract or lower part of the respiratory tract, in particular comprising larynx, windpipe, tracheae, main bronchus (bronchus principalis), bronchi, bronchioles, alveoli (pulmonary vesicles) and lung.

Many of the aforesaid organs are regions of the respiratory tract accessible from outside. In the sense of the present invention, "accessible from outside" means that the organs, in particular their mucous membranes, are accessible by external application or administration of the active substance according to the invention deuterium oxide ($D_2O$), i.e. non-systemically. Thus external administration can for example be effected via an aerosol, i.e. by misting and inhalation of $D_2O$ or by misting and spraying of the organs or regions of the organs with $D_2O$, or by irrigation of the appropriate organs or regions of the organs with $D_2O$ or by administration of liquid $D_2O$ or $D_2O$ gels or $D_2O$ hydrogels. A comprehensive and detailed description of the administration routes of $D_2O$ according to the invention is given below.

Organs or regions of such organs which are to be defined as "accessible from outside" according to the invention are for example the nose, nasal mucous membrane, nasal sinus mucous membrane, mouth, oral mucous membrane, pharynx, pharyngeal mucous membrane, larynx, laryngeal mucous membrane, windpipe, tracheae, tonsils, bronchi, bronchioles, aveoli, lung and the mucous membrane of the windpipe, tracheae, tonsils, bronchi, bronchioles, aveoli and lung.

In the sense of the invention, "viral infection" should be understood to mean the active or passive penetration of a virus into an organism, such as a plant, animal or man, and the reproduction thereof in this organism. Such an organism is described according to the invention as a "host", and includes vertebrates, in particular mammals, above all man, horses, pigs, cattle, goats, sheep, cats and dogs. The cells of such a host are described as "host cells". In the sense of the present invention, an "organism to be treated" is such a host which either suffers from a virus-based disease of the respiratory tract and is therapeutically treated or is prophylactically treated with regard to such a disease, where man here is a particularly preferred host. In the sense of the invention, an "organ to be treated" is an organ of such an organism defined above.

In the sense of the invention, the terms "virus infection", "infection by viruses", "viral infection" and "infection" are used synonymously and all refer to an infection effected by a virus.

Many viruses are known which cause a virus-based disease of the respiratory tract according to the invention. Some of these viruses and their infection route and pathological manifestation, i.e. the disease caused by them, have already been described in more detail in the present specification. Hence a preferred embodiment of the invention relates to the use of deuterium oxide for the prophylaxis and/or therapy of virus-based diseases of the respiratory tract, wherein the virus is a virus of the families Picornaviridae, Orthomyxo-viridae, Paramyxoviridae, Coronaviridae, Adenoviridae and/or Herpesviridae. Particularly preferably, the virus is a virus of the genus *Rhinovirus, Enterovirus, Influenzavirus, Pneumovirus, Metapneumovirus, Coronavirus, Mastadenovirus, Simplex-* virus and/or *Varicellovirus*. Especially preferably, the virus is a virus of the species *rhinivirus*, Cosackie virus-1, Cosackie virus-2, echovirus, polio virus, influenza virus A, influenza virus B, parainfluenza virus, respiratory syncytial virus (RSV), human metapneumovirus, coronavirus, human adenovirus A, human adenovirus B, human adenovirus C, human adenovirus D, human adenovirus E, human adenovirus F, human herpes virus 4 (HHV-4) (Epstein-Barr virus), herpes simplex virus (HSV-1), herpes simplex virus (HSV-2) and/or varicella zoster virus (VZV).

According to the invention, the terms "virus type" and "virus species" are used synonymously.

According to the invention, the terms "prophylaxis and/or therapy" refer to any measure suitable for the treatment of a virus-based disease of the respiratory tract which is either a preventive treatment of a such an emergent disease or of emergent symptoms thereof or of a typical preceding disease or indication (prophylaxis) or the treatment of the disease after onset and/or the avoidance of renewed onset of such a disease, for example after a completed treatment period (therapy).

In general, an effective prophylaxis and/or therapy of a virus-based disease of the respiratory tract is in particular effected by topical or systemic administration of a pharmaceutical active substance or an antiviral active substance.

In the sense of the invention, "topical" or "topical application" or "topical administration" should be understood to mean that a pharmaceutical or antiviral active substance, according to the invention $D_2O$, in contrast to systemic uptake, is taken up not into the bloodstream of the organism to be treated, but is only applied, added or introduced locally, in particular on the surface, onto/into an organ of the respiratory tract to be treated, in particular onto/into epithelial cells and/or mucous membranes thereof, preferably in the form of drops, i.e. in liquid form, for example as irrigation, or in gaseous form as an aerosol or vapor, or in the form of a formulation such as a hydrogel. In the sense of the invention, "systemic" administration should be understood to mean that a pharmaceutical or antiviral active substance is taken up into the bloodstream of the organism to be treated. In principle, topical administration of a pharmaceutical or antiviral active substances is lower in side-effects than systemic administration, since with topical administration high active substance concentrations are only reached locally, i.e. in a defined and limited region of the organ of an organism to be treated, and the whole organism, more precisely its bloodstream, is not exposed to the active substance as is the case with systemic administration.

Such a pharmaceutical active substance or antiviral active substance topically administered for the prophylaxis and/or therapy of a virus-based disease of the respiratory tract should have at least one, preferably several, of the following properties:

a) site-specific usability by topical administration over a period of any length and with high permucosal transport kinetics of the active substance. This is achieved by the targeted transport of the active substance into defined regions of the organ to be treated, in particular into the cells, above all epithelial cells and mucous cells, through the choice of a suitable formulation of the active substance (for example by irrigation or an aerosol).

b) retardation of the transepithelial transport of the active substance into the bloodstream, i.e. into the blood vessels, c) largely homogenous active substance distribution in the region of the site of action (organ to be treated) and the avoidance of local overconcentrations, d) virostatic action, i.e. an action blocking or inhibiting the reproduction of viruses, on the cells in the treated region of the organ (i.e. the viral reproduction by the host cell's own replication apparatus is blocked or inhibited), e) substantial tolerance of the antiviral active substance by the healthy cells (not infected by the virus) in the cutaneous tissue and the bloodstream for the avoidance of side-effects, in particular also with regard to immune reactions.

According to the invention, it was established that deuterium oxide ($D_2O$) displays all the aforesaid properties. Furthermore, $D_2O$ has marked advantages compared to the antiviral active substances known in the state of the art, particularly the virostatic agents, for example lower or no side-effects, increased bioavailability and universal usability on all viruses which cause infections of the respiratory tract.

According to the invention, it was further established that deuterium oxide is an effective antiviral active substance with potential long-term action and is suitable both for short-term, long-term and repeat therapies of virus-based diseases of the respiratory tract. According to the invention, deuterium oxide, also referred to below as $D_2O$, is a pharmaceutical or antiviral active substance.

According to the invention, the term "pharmaceutical active substance" is understood to mean any inorganic or organic molecule, substance or compound which has a pharmacological action. The term "pharmaceutical active substance" is herein used synonymously with the term "drug". In the sense of the invention, pharmaceutical active substances also include antiviral active substances, including $D_2O$.

In the sense of the invention, the term "antiviral active substance" defines an active substance which is administered for the treatment of virus-based diseases and in particular virus-based diseases of the respiratory tract. Preferably such an antiviral active substance is suitable for already inhibiting or blocking the viral infection of the host cell and/or the reproduction of the viral nucleic acid in the host cell and/or the reproduction of the virus. If an antiviral active substance blocks or inhibits viral reproduction, the term "virostatic active substance" is also used. In the sense of the invention, the terms "pharmaceutical active substance" and "antiviral active substance" are used synonymously.

In the sense of the invention, "cells" are vertebrate cells, in particular mammalian cells and above all human cells (cells of man), in fact epithelial cells of the skin, above all dermal cells, mucous cells and mucous membrane cells. According to the invention, "host cells" are cells which have been infected or can be infected by a virus. The defined cells and host cells of the invention are those of the respiratory tract.

The properties of $D_2O$ and the use thereof according to the invention as an antiviral active substance for the prophylaxis and/or therapy of virus-based diseases of the respiratory tract are explained below:

Deuterium oxide ($D_2O$), often also described as "heavy water", is a substance extremely similar in its physical properties to "natural water" $H_2O$. Deuterium oxide ($D_2O$) and water ($H_2O$) differ physically through the substitution of the hydrogen atoms of $H_2O$ by deuterium atoms, as a result of which $D_2O$ has a ca. 10% higher density and ca. 25% higher viscosity. Furthermore, the melting and boiling temperatures of $D_2O$ are higher than for $H_2O$. A detailed comparison of the properties is given in the Handbook of Chemistry and Physics, Section 6 (Handbook of Chemistry and Physics, David R Lide, Editor, $79^{th}$ Edition, 1998 CRC Press, Boca Raton, USA).

In contrast to the physically similar properties of $H_2O$ and $D_2O$, there are significant physiological differences (see inter alia Kushner D J et al., *Pharmacological uses and perspectives of heavy water and denatured compounds*, Can J Physiol Pharmacol. 1999 February; 77(2): 79-88). Beyond a certain concentration in a cell, of more than 20-25% in animal cells, $D_2O$ has an action on enzymatic reactions. Enzymatically controlled reactions are increasingly altered, in particular blocked or inhibited. One reason for this is seen in the higher bond strength of the hydrogen bridge bonds when the hydrogen atom in the bond is replaced by a deuterium atom. Both in aqueous solutions of $H_2O$ and $D_2O$ and also in the binding of water to organic molecules, this higher bond strength arises (Cuma M, Scheiner S, Influence of Isotopic Substitution on Strength of Hydrogen Bonds of Common Organic Groups, Journal of Physical Organic Chemistry, 1997, Vol. 10, 383-395). This increased bond strength of hydrogen bridge bonds (H bridges) in the case where the hydrogen atom of the bond is replaced by a deuterium atom and the decreased rate of exchange of $D_2O$ compared to $H_2O$ (Konig S et al., Molecular dynamics of water in oriented multilayers studied by quasi-elastic neutron scattering and deuterium-NMR relaxation. 1994, J. Chem. Phys. 100, 3307-3316) has two direct consequences for the binding of $D_2O$ to binding sites suitable for H bridges: a) the probability of presence of $D_2O$ on surfaces with binding possibilities for H bridges is markedly increased compared to that of $H_2O$, and b) the hydratation of the surfaces mentioned in a) increases and the detachment of $D_2O$ (e.g. by evaporation) is energetically impeded, which in turn increases the sustainability of the hydratation.

According to the invention "hydratation" (also known as hydration) should be understood to mean the deposition of $D_2O$ molecules instead of or in addition to $H_2O$ molecules onto a given surface, namely the organ of the respiratory tract to be treated. A hydratation in the sense of the invention can also be described as $D_2O$ hydratation.

According the invention, "degree of hydratation" or "hydratation level" is the time-averaged number of $D_2O$ molecules maximally binding via H bridges onto a given surface, namely the organs of the respiratory tract to be treated, instead of or in addition to $H_2O$ molecules. In the sense of the invention, degree of hydratation or hydratation level can also be referred to as $D_2O$ degree of hydratation or $D_2O$ hydratation level.

Herein, "sustainability of the hydratation" should be understood to mean the activation energy for the detachment of a $D_2O$ molecule or $H_2O$ molecule bound by H bridges from a surface, namely the organ of the respiratory tract to be treated, a higher activation energy meaning higher sustainability. The sustainability of the hydratation in the sense of the invention can also be referred to as sustainability of the $D_2O$ hydratation.

As organs (to be treated) of the respiratory tract defined according to the invention, the mucous membranes are examples of particularly strongly hydratized membrane surfaces, wherein the number of the H bridge binding possibilities is massively increased compared to other membranes (e.g. the skin surface) owing to the presence of glycolipids and glycoproteins. In this case, a slight increase in hydratation and/or the sustainability of the hydratation has particularly significant consequences which has an advantageous effect on the use of $D_2O$ according to the invention.

It is common specialist knowledge that a cell takes up different quantities of $H_2O$ depending on the level of its metabolic activity at the time. A cell which is infected by a virus, a so-called host cell, and wherein reproduction of the virus is taking place has a far higher metabolic activity than a non-infected cell of the same cell type of the surrounding region. The reason for this is that the host cell is effecting not only its own replication, but also the replication of the virus. Since a higher metabolic activity of cells correlates with an increased water uptake, virus-infected host cells take up markedly more water ($H_2O$) than non-infected cells. Owing to the similar physical properties of $H_2O$ and $D_2O$, $D_2O$ is taken up by cells in parallel to $H_2O$ (if $D_2O$ and $H_2O$ are available) or instead of $H_2O$ (if only $D_2O$ is available).

Action of $D_2O$ on the Replication and Reproduction of a Virus

As described above, it is known that enzymatic reactions in a cell can be altered by $D_2O$ at sufficient concentration. As explained above, cells, and to an increased extent virus-infected cells, take up $D_2O$ in parallel to or instead of $H_2O$. Hence if $D_2O$ is administered to a virus-infected cell at a "sufficient concentration" according to the invention, i.e. more than 20% based on the total water content of a cell, this results in blockade or inhibition of enzymatic reactions in the host cell. This includes in particular the blockade or inhibition of DNA polymerase (Takeda H et al. Mechanisms of cytotoxic effects of heavy water (deuterium oxide: $D_2O$) on cancer cells, Anticancer Drugs 1988 September; 9(8), 715-25). As a result of this, the DNA replication in a cell is blocked or inhibited. Non-infected, healthy cells in the region (area) surrounding the virus-infected cells take up $D_2O$ or $H_2O$ to a normal extent on account of their lower metabolic activity in comparison to infected cells, so that no or only very slight, negligible blockade or inhibition of enzymatic reactions takes place in these.

According to the invention, it has now been established that if a cell is infected with a virus (host cell), the viral DNA is also not replicated owing to the blockade or inhibition of the host cell's own DNA polymerase, since the replication thereof also takes place through the involvement of the host cell DNA polymerase. In the case of RNA viruses, the enzymatic blockade or inhibition by $D_2O$ also takes place for synthesis of the reverse transcriptase encoded by virus genes, which must first be synthesized in the host cell in order to transcribe the viral RNA into viral DNA, which is then in turn replicated by the DNA polymerase of the host cell. Thus blockade or inhibition of certain enzymatic reactions of the host cell by $D_2O$ also blocks or inhibits the replication and thus also the subsequent reproduction (as defined above) of a virus after a viral infection.

Action of $D_2O$ on the Cell Division of Virus-Infected Cells

A further important aspect of the invention, which is based on said elevated binding property of $D_2O$, is that on administration of $D_2O$ at sufficient concentration, i.e. more than 20%, based on the total water content of a cell, cell division is blocked or inhibited. This most probably occurs, in addition to the stated blockade or inhibition of DNA replication, through the blockade or inhibition of mitosis in the animal cell division cycle (Laissue J A et al. *Survival of tumor-bearing mice exposed to heavy water or heavy water plus methotrexate.* Cancer Research, 1982, Vol. 42 (3) 1125-1129). According to the invention, this is of decisive importance for the latency state in virus-based diseases of the respiratory tract in which the viruses are present in the resting state (latency) during the lysogenic cycle described in more detail above. In this state, the viral genome is integrated into the host cell genome and transmitted to the host cell progeny together with the host genome on division of the host cell. Thus with blockade or inhibition of the cell division, transmission of the virus to new cells is prevented.

A blockade or inhibition of viral reproduction is thus effected according to the invention by the use of $D_2O$ for the prophylaxis and/or therapy of virus-based diseases of the respiratory tract. This blockade or inhibition of the viral reproduction by $D_2O$ as an antiviral active substance takes place according to the invention in particular by:

the blockade or inhibition of the replication of the viral nucleic acid and hence the reproduction of the virus and/or the blockade or inhibition of host cell division and hence of the reproduction of the virus in the lysogenic cycle.

The term "block" or "blockade" according to the invention should be understood to mean that the replication of viral nucleic acids (viral RNA or viral DNA), viral reproduction and/or the cell division rate of host cells of the invention is retarded and/or decreased, preferably up to 6%, preferably up to 10%, preferably up to 15%, also preferably up to 20%, more preferably up to 25%, more preferably up to 30%, also more preferably up to 35%, also more preferably up to 40%, also more preferably up to 45%, also more preferably up to 50%, still more preferably up to ca. 55%, still more preferably up to ca. 60%, even more preferably up to 65%, also more preferably up to 70%, also more preferably up to 75%, also more preferably up to 80%, also more preferably up to 85%, still more preferably up to 90%, and most preferably up to 94% compared to the replication or reproduction rate of the virus or the host cell division rate without administration of $D_2O$.

The term "inhibit" or "inhibition" according to the invention means that the replication of viral nucleic acids (viral RNA or viral DNA), viral reproduction and/or the cell division rate of host cells of the invention is prevented, preferably up to 95%, still more preferably up to 98% and most preferably up to 100% (and hence completely), compared to the replication or reproduction rate of the virus or the host cell division rate without administration of $D_2O$.

Such an antiviral and virostatic action of $D_2O$ based on the blockade or inhibition of the replication of virus nucleic acids (viral nucleic acids) and/or viral reproduction has not previously been described in the state of the art.

In addition, $D_2O$ has considerable advantages compared to known antiviral and virostatic active substances for the treatment of virus-based diseases of the respiratory tract, namely above all the following properties of $D_2O$:

1) $D_2O$ is not virus-specific and can block or inhibit the replication and/or reproduction of all viruses described according to the invention. This is particularly advantageous since most virus-based diseases of the respiratory tract, as described above, can be triggered by various viral species (also known as viral types) and in addition cannot be distinguished symptomatically. Hence $D_2O$ as a so-called "broad band" virostatic agent can be administered for the prophylaxis and/or therapy of all virus-based diseases of the respiratory tract.

2) Through the topical administration of $D_2O$ according to the invention, e.g. by inhalation of an aerosol or by irrigation with a $D_2O$ solution, a concentration high enough for therapeutic effectiveness (i.e. more than 20% based on the total water content of a cell) of $D_2O$ can be attained in the epithelial cells of the organs of the respiratory tract to be treated, without other, non-virus-infected organs of the organism being exposed to similarly high concentrations of $D_2O$, as occurs with systemic administration. Hence a critical problem discussed in the state of the art, for the attainment of therapeutically effective $D_2O$ concentrations at the site of action (i.e. more than 20% based on the total water content of a cell) without severe side-effects to other, healthy organs or healthy surrounding tissue, is solved.

3) According to the invention, the physical state of $D_2O$ for topical administration is liquid or gaseous, or it is present in a solid formulation, such as an ointment, cream, gel or hydrogel. The $D_2O$ is taken up by the epithelial cells of the respiratory tract by direct contact of the liquid $D_2O$ or a $D_2O$-containing formulation or a $D_2O$-containing aerosol.

4) Particularly for the case where $D_2O$ is administered as an aerosol, it should be stated that $D_2O$ aerosols have a unique advantage over all other liquid aerosolizable pharmaceutical active substances. While in all other cases additives must be added in order to transport the active substance stably into the respiratory tract via the aerosol, this is not necessary with $D_2O$, since it is already optimally aerosolizable as a pure molecule with no additives. Segregation affecting efficacy in the respiratory tract, such as can occur with other substance mixtures (of active substance and additive(s)) during aerosolization and side-effects caused by the additives is thus ruled out. "Aerosolizable" and "aerosolizability" should be understood to mean the basic possibility of converting a substance into an aerosol of controllable particle size by methods which are known in the state of the art.

5) For the case where pure liquid $D_2O$ is administered alone (pure $D_2O$), it should be stated that $D_2O$ has a unique advantage over all other liquid pharmaceutical active substances. It can be transported into the epithelial cells of the respiratory tract like normal water ($H_2O$) and furthermore by the strength and direction of the osmotic gradients and manipulation of these two quantities the penetration depth of $D_2O$ into the epithelial cells can be suited to the therapeutic objective.

6) As already described, the hydrogen bridge bond strength of deuterium atoms is higher than with hydrogen atoms, particularly in the binding of water to organic molecules. Topically administered $D_2O$ binds molecularly via hydrogen bridge bonds to the nearest available cell surface and thereby displaces the $H_2O$ absorbed there owing to its higher bond strength. The exchange frequency of the $D_2O$ molecules with the $H_2O$ environment is in turn somewhat slower than for $H_2O$ owing to this higher bond strength (and owing to the higher weight of the $D_2O$ molecule) (Konig S et al., *Molecular dynamics of water in oriented multilayers studied by quasi-elastic neutron scattering and deuterium-NMR relaxation.* 1994, J. Chem. Phys. 100, 3307-3316). This results in an increased probability of presence of the $D_2O$ molecules directly on the cell surface, connected with increased internalization of $D_2O$ in the cell, as a result of which it can exert its action—the blockade or inhibition of the aforesaid enzymatic reactions of a virus-infected host cell and the division thereof. Since virus-infected cells have a higher uptake capacity for water or $D_2O$ than normal cells, it is also ensured that $D_2O$ is enriched disproportionately in these cells compared to healthy cells, i.e. in a sufficient $D_2O$ concentration of more than 20% based on the total water content of the cell. Owing to these properties, the topical administration of $D_2O$ is of exceptional value.

7) $D_2O$ is the only non-radioactive molecule which is very similar to $H_2O$ in its properties. Cells in general, and in particular the cells according to the invention, cannot "distinguish" between the two molecules, so that $D_2O$ is transported into the cell and reaches the cell nucleus by active and passive transport in the same way as $H_2O$. As a result, cell barriers of any kind which prevent the penetration of other pharmaceutical active substances are circumvented and defense mechanisms at the cellular level, such as internalization in lysosomes or the activation of MDR (multiple drug resistance) transporters or at the organ level through the immune system, which could reduce or inhibit the efficacy of the pharmaceutical active substance $D_2O$ are also largely turned off.

8) A further advantage of $D_2O$ as an antiviral or virostatic active substance is the fact that concentrations of less than 20% $D_2O$ (based on the total water content of the cell) in the cell exert no significant effects and hence normal cells which take up comparatively little $D_2O$ owing to their lower water permeability and/or water uptake compared to the active, virus-infected cells, are scarcely exposed to the effects of the $D_2O$.

In a particularly preferred embodiment of the present invention, according to the invention $D_2O$ is administered non-systemically.

A particularly preferred embodiment of the invention is the use of deuterium oxide for the prophylaxis and/or therapy of virus-based diseases of the respiratory tract, wherein the deuterium oxide is administered topically. Such topical administration is preferably effected in the form of drops, i.e. in liquid form, such as for example by irrigation, or in gaseous form as an aerosol or vapor, or in the form of a formulation, such as a hydrogel. Above all, side-effects which are caused by systemic administration of antiviral or virostatic active substances are thereby avoided.

A further particularly preferred embodiment of the invention is the use of deuterium oxide wherein the deuterium oxide hydratizes the respiratory tract, or the organs of the respiratory tract to be treated, in particular the mucous membranes of the respiratory tract, above all the nasal mucous membrane.

By direct administration according to the invention onto virus-infected organs or organs of the respiratory tract to be treated, in particular the mucous membranes of the respiratory tract, such as the nasal mucous membrane, locally prophylactically or therapeutically effective $D_2O$ concentrations and locally prophylactically or therapeutically effective hydratization with $D_2O$ can be attained and at the same time stresses to the system (i.e. the bloodstream) and the side-effects on healthy tissue and organs of the respiratory tract not to be treated and tissue of other organs (such as for example the liver or kidneys, which could be caused by a high concentration of $D_2O$ of more than 20% $D_2O$, based on the total water content of the cell) can be decreased or completely avoided. Furthermore, transport of $D_2O$ into the system can be prevented or limited by means which are well known in the state of the art. Inter alia, examples of these means are the deliberate manipulation of the osmotic gradients across the mucous membrane (i.e. between the systemic part and the mucous membrane surface) by decreasing the water potential of the administered $D_2O$ by means of substances which are suitable for altering this water potential, in particular physiologically compatible salts such as sodium chloride, water-soluble polymers and other non-pharmaceutical substances.

According to the invention, $D_2O$ can be used alone as a pharmaceutical active substance, more precisely as an antiviral or virostatic active substance, or in combination with one or more other pharmaceutical active substance(s) and/or one or more other non-pharmaceutical active substance(s) (which can in particular be used for optimizing the topical administration of $D_2O$ as a pharmaceutical active substance on the mucous membranes).

Hence a preferred embodiment of the present invention relates to the use of deuterium oxide for the prophylaxis and/or therapy of virus-based diseases of the respiratory tract wherein the $D_2O$ is used in combination with at least one other pharmaceutical active substance and/or at least one other non-pharmaceutical active substance.

Such a combination of $D_2O$ and at least one other pharmaceutical active substance and/or at least one other non-pharmaceutical active substance is referred to below as a "combination according to the invention".

All the uses and administrations of $D_2O$ according to the invention, for example as formulation, liquid, hydrogel, vapor or aerosol or in a solvent, topically, etc. disclosed in this specification are also usable without restriction for a combination according to the invention, unless the contrary is indicated. The same applies for the use and administration of $D_2O$ in combination with $H_2O$, also referred to below as "mixture of $D_2O$ and $H_2O$".

A further preferred embodiment of the present invention relates to the use of deuterium oxide for the prophylaxis and/or therapy of virus-based diseases of the respiratory tract, wherein the $D_2O$ is used in combination with at least one other pharmaceutical active substance, this being selected from the group consisting of virostatic agents, sympathomimetic agents, in particular alpha sympathomimetic agents, proteins, peptides, nucleic acids and immuno-suppressant active substances.

Below, other preferred pharmaceutical active substances according to the invention of a combination according to the invention and the action thereof are described, however this enumeration is only by way of example and the present invention is not restricted thereto:

Virostatic Agents

Active substances which block the reproduction of viruses are described as virostatic agents. Virostatic agents block the activity of enzymes, for example DNA polymerase, reverse transcriptase or proteases, and thus block or inhibit the replication of the virus or the processing of a synthesized long viral protein into smaller protein segments. Examples of these are amantadine and rimantadine.

Sympathomimetic Agents

Sympathomimetic agents are classified into direct and indirect sympathomimetic agents. Direct sympathomimetic agents activate alpha and/or beta adrenoreceptors by imitating the action of the physiological transmitters adrenalin and noradrenalin. Direct sympathomimetic agents are subdivided into alpha sympathomimetic agents and beta sympathomimetic agents, however there are also active substances which bind to both receptors. Alpha sympathomimetic agents are alpha adrenergic antagonists which bind selectively to alpha adrenoreceptors, and are as a rule mainly used locally in nasal sprays in order to effect a narrowing of the blood vessels in the mucous membranes and a decrease in swelling of the nasal mucous membrane, in particular in rhinitis.

Examples of active substances are naphazoline, tetryzoline, xylometazoline, oxymetazoline and phenylephrine. Indirect sympathomimetic agents increase the concentration of the physiological transmitters in the synaptic cleft. Examples are ephedrine, which causes dilation of the bronchi and stimulation of the circulation, and amphetamine and derivatives thereof, e.g. methylphenidate and MDMA.

Immunosuppressant Active Substances

Through the addition of immunosuppressant active substances, for example corticoids and/or other immunomodulators, the reaction of the epithelial or dermal tissue to the reproduction of the viruses, particularly where inflammation is already present, can be improved and optimized.

Proteins

Proteins usable according to the invention should be understood to mean proteins which intervene appropriately in the infective, replication or reproductive cycle of the virus in a host cell. In this connection, appropriately means that the proteins block, preferably inhibit, the adsorption of the virus onto the host cell, the injection of the viral nucleic acid into the host cell, the replication of the DNA of the host cell or of the nucleic acid of the virus, the processing of the viral nucleic acid or assembly of the viral particles to a complete virus, or intervene in the reproductive cycle of the virus in another way. Examples of these are protease blockers, uncoating blockers, penetration blockers, reverse transcription blockers and DNA polymerase blockers.

Peptides

Peptides usable according to the invention should for example be understood to mean peptides which appropriately influence, in particular increase, the membrane permeability of the host cell membranes. Thereby, improved transport of $D_2O$ and optionally of the other pharmaceutical or the non-pharmaceutical active substances of the invention into the host cell can be achieved. An example of this is melittin. In addition, all peptides which have actions analogous to those described above for proteins should be understood to be peptides usable according to the invention.

Nucleic Acids

Through the addition of nucleic acids, in parallel to the antiviral or virostatic action of $D_2O$, a modification of the genetic information of the cells in the region of the site of action or a deliberate switching off ("gene silencing") of certain genes, for example of the DNA polymerase, of cells in the region of the site of action, i.e. of the organ of the respiratory tract to be treated, and hence a modification of the proteome, can be achieved. The "gene silencing" can for example have the result that the genes involved in DNA damage defense (for example p53, BRCA1, BRCA2, ATM, CHK2) are switched off and hence the viruses whose reproduction has been prevented by $D_2O$ in the cells no longer revert to a latent stage even in the long term (after the end of the topical $D_2O$ administration), but are long-term prevented from expressing viral DNA. Methods for effecting "gene silencing" are well known to the person skilled in the art and described for example in Mello C C, Conte D, "Revealing the world of RNA interference" in Nature 431, 338-342 (16 Sep. 2004). Preferably the nucleic acids are DNA, preferably oligonucleotides, sense or antisense DNA, natural or synthetic, cDNA, genomic DNA, naked DNA, single or double strand DNA, or circular DNA, or RNA, preferably antisense RNA, RNAi, siRNA or other RNA molecules suitable for the interference, which are not restricted as to their length.

The concentration of other pharmaceutical active substances used as well as $D_2O$ as a pharmaceutical active substance according to the invention based on the whole solution of a combination according to the invention lies in the range from at least $10^{-8}$ M to at least $5 \times 10^{-2}$ M, preferably from at least $10^{-7}$ M to $10^{-3}$ M, most preferably from at least $10^{-6}$ M to at least $10^{-2}$ M. An especially preferable concentration range lies in the range from at least $10^{-9}$ M to at least $10^{-2}$ M.

A likewise preferred embodiment of the present invention relates to the use of deuterium oxide for the prophylaxis and/or therapy of virus-based diseases of the respiratory tract, wherein the $D_2O$ is used in combination with at least one other non-pharmaceutical active substance, this being selected from the group consisting of pharmaceutically compatible inorganic or organic acids or bases, polymers, copolymers, block copolymers, simple sugars, complex sugars, ionic and nonionic surfactants or lipids and mixtures thereof, albumin, transferrin and DNA repair proteins, such as kinase inhibitors.

In the sense of the invention, the term "non-pharmaceutical active substance" refers to any pharmacologically compatible and therapeutically useful molecule, substance or compound which is not a pharmaceutical active substance but is administered to an organism to be treated, preferably with at least one pharmaceutical active substance according to the invention, for example formulated in a formulation according to the invention, in order to influence, in particular to improve, qualitative properties of the pharmaceutical active substance/ substances. Preferably, the non-pharmaceutical active substances exert no or no appreciable or at least no undesired pharmacological action with regard to the intended prophylaxis or therapy of virus-based diseases of the respiratory tract. Examples of suitable non-pharmaceutical active substances are pharmacologically harmless salts, for example sodium chloride, aromas, vitamins, e.g. vitamin A or vitamin E, tocopherols or similar vitamins or provitamins occurring in the human body, antioxidants such as for example ascorbic acid, and stabilizers and/or preservatives to prolong the use and storage period of a pharmaceutical active substance or a formulation according to the invention and other usual non-pharmaceutical active substances or excipients and additives known to the person skilled in the art.

Below, other preferred non-pharmaceutical active substances according to the invention of a combination according to the invention and their action and suitable concentrations are described, however this enumeration is only by way of example and the present invention is not restricted thereto:

Water-Soluble Excipients and Additives

By addition of water-soluble excipients and additives, such as for example pharmaceutically compatible inorganic or organic acids, bases, salts and/or buffer substances for adjusting the pH value, the physiological compatibility of $D_2O$ in the cells of the organs of the respiratory tract can be improved for non-virus-infected cells. Examples of preferred inorganic acids are selected from the group consisting of hydrochloric acid, hydrobromic acid, nitric acid, sulfuric acid and phosphoric acid, hydrochloric acid and sulfuric acid being particularly preferred. Examples of particularly suitable organic acids are selected from the group consisting of malic acid, tartaric acid, maleic acid, succinic acid, acetic acid, formic acid and propionic acid and particularly preferably ascorbic acid, fumaric acid and citric acid. Optionally, mixtures of said acids can also be used, in particular of acids which as well as their acidic properties also have other properties, e.g. in use as anti-oxidants, such as for example citric acid or ascorbic acid. Examples of pharmaceutically compatible bases are alkali metal hydroxides, alkali metal carbonates and alkali metal ions, preferably sodium. Mixtures of these substances can in particular be used for the adjustment and buffering of the pH value, and particularly preferable for this are potassium hydrogen phosphate and dipotassium hydrogen phosphate, sodium hydrogen phosphate and disodium hydrogen phosphate and citric acid and sodium citrate. Other preferred buffer substances in the sense of the invention are PBS, HEPES, TRIS, MOPS and other physiologically compatible buffer substances, in particular those with a pK value in the range 4.0 to 9.0. The concentration of these substances, based on the total solution of a combination according to the invention preferably lies in the range from micromolar to millimolar, particularly preferably in the range 1-100 mM.

Water-Soluble Polymeric Molecules

By addition of water-soluble, non-cytotoxic molecules, such as for example certain polymers (e.g., but not limited thereto, dextran, polyethylene glycol, agarose, cellulose, acrylic acid and hyaluronic acid), copolymers and block copolymers, an additional delay (retardation) in the transfer of the $D_2O$ into the epithelial cells of the respiratory tract on topical administration and also from the epithelial cells into the system (bloodstream) can be achieved through their high water-binding capacity. In addition, through the ability of the polymers to lower the chemical potential (water potential) of $D_2O$, the strength and direction of the osmotic gradient across the skin can be modified or improved and optimized. The concentration of these substances, based on the total solution, lies in the range from micromolar to molar, preferably in the range 1-500 mM.

Water-Soluble Non-Polymeric Molecules

By addition of water-soluble, non-polymeric molecules which modify the density and/or viscosity of $D_2O$, for example, but not limited thereto, simple sugars and complex sugars, in particular glucose, sucrose, dextrose, maltose, starch and cellulose, the osmotic conditions in the region of the topical $D_2O$ administration and the $D_2O$ transport and the $D_2O$ retention in the epithelial cells of the respiratory tract can be modified or optimized. The concentration of these substances, based on the total solution of a combination according to the invention, preferably lie in the range from millimolar to molar, particularly preferably in the range 1.0 mM to 1.5 M.

$D_2O$ Interfacial Tension-Modifying Molecules

By addition of substances which modify the interfacial tension of $D_2O$, for example, but not limited thereto, ionic and nonionic surfactants or lipids, in particular a mixture of surfactants and lipids, the transport of the $D_2O$ into the epithelial cells of the respiratory tract on topical administration and within these epithelial cells can be modified. The concentration of these substances, based on the total solution of a combination according to the invention, preferably lies in the range from micromolar to millimolar, particularly preferably in the range 0.05 to 500 mM.

Water-Soluble Non-Cytotoxic Molecules

By addition of water-soluble molecules which are known to be taken up to an exceptional extent by metabolically especially active cells, such as for example virus-infected cells, for example albumin or transferrin, an additional increase in the $D_2O$ transport rate of the molecules surrounded by a $D_2O$ hydrate shell into the target cells of the respiratory tract can be achieved.

The concentration or dosage of $D_2O$ and optionally of the at least one other pharmaceutical and/or non-pharmaceutical active substance depends on various factors, for example the nature of the treatment, nature of the disease, disease state of the patient (mammal), nature of the active substance and the like. Such parameters are known to the person skilled in the art and the determination of the specific dosages is governed by the specialist knowledge of the person skilled in the art. Suitable concentration information is disclosed herein. Some information on suitable concentration ranges is already given above by way of example, however these are only intended as guide values.

The $D_2O$ usable according to the invention is preferably present as liquid. The $D_2O$ is preferably present in a solution, preferably with $H_2O$ (water) as solvent, and is also described herein as "mixture of $D_2O$ and $H_2O$" or "$D_2O/H_2O$" if water is contained, or as "$D_2O$ solution" or "pure $D_2O$" if no water is contained. Pure $D_2O$ preferably contains $D_2O$ in a concentration range of 98.0 to 100%, preferably 98.5 to 99.9%, particularly preferably 99.7% based on the total water content of the solution. A mixture of $D_2O$ and $H_2O$ according to the invention preferably contains $D_2O$ in a concentration range of 1 to 99%, preferably 5 to 95%, more preferably 10 to 90%, also preferably 15 to 80%, more preferably 20 to 70%, also more preferably 30 to 60%, most preferably 40 to 50%, where this information is based on the total water content of the mixture of $D_2O$ and $H_2O$. The preparation of a $D_2O$ solution according to the invention and analogously thereto a combination according to the invention is for example effected by mixing of the components, in particular of $D_2O$ and optionally $H_2O$ and optionally of the at least one other pharmaceutical and/or non-pharmaceutical active substance. Further, optionally a solvent can be added by mixing, as described below. The admixture of $H_2O$ or of the at least one other pharmaceutical and/or non-pharmaceutical active substance or of the solvent to $D_2O$ is preferably effected in the liquid state. However, the preparation can be achieved by any suitable process. In the case where $D_2O$ is used alone (i.e. not in combination with $H_2O$ or at least one other pharmaceutical and/or non-pharmaceutical active substance) and at a concentration of 100% or ca. 99.9% based on the total volume of the solution (i.e. pure $D_2O$), pure $D_2O$ is the $D_2O$ solution according to the invention.

All the uses and administrations of $D_2O$ according to the invention, for example as a formulation, liquid, hydrogel, vapor or aerosol or in a solvent, topically etc., disclosed in this specification are also applicable without restriction to a mixture of $D_2O$ and $H_2O$ according to the invention, unless the contrary is indicated. Also, uses and administrations of a combination according to the invention can be applied without restriction to a mixture of $D_2O$ and $H_2O$ according to the invention, and vice versa, unless the contrary is indicated.

In a preferred embodiment, the at least one other pharmaceutical or other non-pharmaceutical active substance is bound to $D_2O$. In the sense of the present invention, "bound" means that the pharmaceutical or non-pharmaceutical active substance is hydratized by the $D_2O$.

In a further preferred embodiment, the $D_2O$ or the combination according to the invention is contained in a suitable solvent. A solvent according to the invention can be an inorganic or organic solvent. Suitable solvents of the present invention should preferably be physiologically well tolerated by the organism (in particular mammal) to which the active substance with solvent is administered, i.e. trigger no side-effects, e.g. toxic side-effects. A particularly preferred solvent is distilled water. Also preferred are ethanol-water mixtures; here the percentage mass content of ethanol in these mixtures is preferably in the range between 5% and 99% ethanol, also preferably in the range from 10% to 96% ethanol, more preferably between 50% and 92%, and most preferably between 69% and 91% ethanol.

$D_2O$ or a combination according to the invention or a mixture of $D_2O$ and $H_2O$ according to the invention can be present "preformulated", for example packed in suitable means for the transport of pharmaceutical active substances, so-called "drug delivery" systems, for example in nanoparticles, vectors, preferably gene transfer vectors, viral or non-viral vectors, poly- or lipoplex vectors, liposomes or hollow colloids (i.e. hollow spheres of colloidal size). Also suitable for the transport are naked nucleic acids, in particular naked DNA. Suitable vectors, liposomes, hollow colloids or nanoparticles and processes for the introduction of substances into such vectors, liposomes, hollow colloids or nanoparticles are generally well known in the state of the art and for example described in Cryan S-A, Carrier-based strategies for Targeting Protein and Peptide Drugs to the Lungs, AAPS Journal, 2005, 07(01): E20-E41 and Sambrook et al. Molecular Cloning A Laboratory Manual, Cold Spring Harbor Laboratory (1989) NY. As gene transfer vectors, polyethylen-imine or cationic lipids such as for example DOTAP can preferably be used. Liposomes are preferably usable for the packing of cytostatic agents; a detailed description is for example given in Koshkina N V et al., Paclitacel liposome aerosol treatment induces inhibition of pulmonary metastases in murine renal carcinoma model., Clinical Cancer Research, 2001, 7, 3258-3262. Proteins as pharmaceutical active substances can preferably be packed in biocompatible poly-lactic/glycolic acid polymers (PLGA) by means of super-critical liquids, emulsion processes and spray drying.

According to the invention, $D_2O$ is preferably administered topically. This is effected by application, addition or introduction of $D_2O$ onto/into the epithelial cells or mucous membranes of the organ of the respiratory tract to be treated preferably in the form of drops, i.e. in liquid form, such as for example as irrigation, or in gaseous form as an aerosol or vapor, or in the form of a formulation such as a hydrogel. The nature and duration of the topical administration of $D_2O$ for the prophylaxis and/or therapy of virus-based diseases of the respiratory tract and the concentration of the $D_2O$ and if necessary of other pharmaceutical and/or non-pharmaceutical active substances is dependent on the severity of the disease and the patient's condition and also on the location and accessibility of the organ of the respiratory tract to be treated.

A preferred embodiment of the invention relates to the use of deuterium oxide for the prophylaxis and/or therapy of virus-based diseases of the respiratory tract wherein the $D_2O$ is administered as an aerosol. The aerosol is administered topically, by being inhaled or sprayed.

"Aerosol" is understood to mean solid or liquid suspended particles with a diameter of ca. 0.0001 µm to ca. 100 µm in gases, in particular air, wherein the composition and form of the aerosols can vary very greatly. The smallest pharmaceutically active particles in aerosols are for example nucleic acids, peptides or proteins, and the largest particles are for example mist particles. Aerosols often consist of mixtures of particles of different particle sizes and hence embody a polydisperse size distribution. Aerosols can be produced artificially by dispersion and condensation processes well known in the state of the art. They can be used with no propellant or in combination with a liquefied gas as the propellant, for example in spray-cans.

The use of $D_2O$ as an aerosol according to the invention is preferably effected either via a "nebulizer" or a "pump spray", depending on the location of the organ of the respiratory tract to be treated and thus the site of the viral infection.

"Nebulizer" for the present invention should be understood to mean any apparatus suitable for medicinal aerosols, with which aerosol particles in the size range 50 nm to 500 µm can be produced. The nebulizer sprays a defined volume of the $D_2O$, mostly with the use of high pressures, through small nozzles in order thus to create an aerosol applicable onto the organs of the respiratory tract to be treated, in particular onto the epithelial cells and mucous membranes thereof, in particular of the lower respiratory tract. $D_2O$ can above all, but without restriction thereto, be used for the treatment of virus-based diseases of the lower respiratory tract, such as for example pharyngitis, laryngitis, bronchiolitis, bronchitis, alveolitis and pneumonia.

Suitable nebulizers also include propellant-driven inhalation devices or nebulizers. Propellants here can for example be CFCs or HFCs. Concerning this, reference is made to "Theory and Practice of Inhalational Therapy", pages 31 to 70, Arcis Verlag (2000), where a detailed description of usable nebulizers and methods for their use is/are disclosed.

Examples of nebulizers suitable according to the invention are compressed air-driven nozzle nebulizers (e.g. PARI LC plus, PARI GmbH, Starnberg, Germany), venturi nozzle nebulizers, steam-driven nozzle nebulizers or ultrasound nebulizers (e.g. AeronebLab, Aerogen Inc., Stierlin Court, Canada; eFLOW, PARI GmbH, Starnberg, Germany). Also suitable are nebulizers of a size which can be carried by the (human) patient, e.g. the Respimat@, as described in WO 97/12687. All references cited herein are incorporated into the present invention in their entirety.

In the sense of the present invention, a pump spray is understood to mean a medical device with which larger aerosol particles with a diameter of 100 nm to 1000 μm can be created. This is achieved by accelerating the $D_2O$ under pressure through a nozzle with predefined holes. Since the aerosol particles which are created with a "pump spray" are larger than those from the nebulizer, they already deposit in the mouth, pharynx and nose. Hence the pump spray can be used in particular, but not restricted thereto, for the local administration of $D_2O$ into the upper regions of the respiratory tract such as the mouth, pharynx, tonsils and nose for the treatment of virus-based diseases of the lower respiratory tract such as rhinitis, sinusitis, tonsillitis, angina lateralis, herpangina, herpes nasalis, gingivo-stomatitis herpetica and apthosis herpetica.

In addition, the production of an aerosol usable according to the invention can be effected by any other suitable known standard techniques for aerosol production.

The $D_2O$ concentrations to be used for the use of $D_2O$ as an aerosol according to the invention are dependent on various factors, for example the use purpose, severity of the disease and the patient's condition, and depend on the specialist knowledge of the person skilled in the art. Preferably, an aerosol according to the invention contains $D_2O$ in a concentration range of 1 to 98 wt. %, preferably 10 to 90 wt. %, also preferably 15 to 80 wt. %, more preferably 20 to 70 wt. %, also more preferably 30 to 60 wt. % and most preferably 40 to 50 wt. %.

A preferred embodiment of the invention relates to the use of deuterium oxide for the prophylaxis and/or therapy of virus-based diseases of the respiratory tract wherein the $D_2O$ is administered as a formulation. The formulation is topically administered by application onto the organ of the respiratory tract to be treated, in particular onto the epithelial cells or mucous membrane thereof. A formulation according to the invention is preferably a liquid or a hydrogel.

Such a "liquid" or liquid formulation in the sense of the invention includes formulations of pure $D_2O$, of a mixture of $D_2O$ and $H_2O$ and of a combination according to the invention, insofar as this is in the liquid state. It is preferably administered in the form of drops or by irrigation.

Formulations according to the invention, also described as $D_2O$ formulations, are suitable for the treatment of virus-based diseases of both the upper and also the lower respiratory tract. They are applied topically onto the organ to be treated, in particular onto the epithelial cells or mucous membranes thereof. For this, they are preferably administered as vapor, liquid, preferably by irrigation or drops, cream, ointment, gel or hydrogel:

- $D_2O$ is applied as vapor onto the organ to be treated, in particular the epithelial cells or mucous membranes thereof, by suitable methods known from the state of the art. This administration form is particularly suitable for the treatment of virus-based diseases of the lower respiratory tract.
- $D_2O$ irrigation is used for the irrigation of the nose, mouth and pharynx. In this way, $D_2O$ can be applied and introduced topically and in high concentrations onto the organ to be treated, in particular the epithelial cells or mucous membranes thereof. $D_2O$ irrigation is preferably used for the prophylaxis and/or therapy (treatment) of rhinitis, sinusitis, tonsillitis, angina lateralis, herpes nasalis, gingivostomatitis herpetica and apthosis herpetica. $D_2O$ irrigation is for example particularly suitable for the treatment of rhinitis sicca.

D₂O nasal drops can be used for direct local administration of the D₂O onto the organ to be treated, in particular the epithelial cells or mucous membranes thereof, such as the nose and nasal mucous membrane, preferably for the treatment of rhinitis and sinusitis. For this, D₂O nasal drops are dripped into the nose and transported into the upper nasal regions by strong inhalation. D₂O nasal drops are for example particularly suitable for the treatment of rhinitis sicca.

D₂O cream, D₂O ointment, D₂O gel and D₂O hydrogel are applied and introduced topically onto the organ to be treated, in particular the epithelial cells or mucous membranes thereof, preferably onto the mucous membranes in mouth and nose and are in particular used for the treatment of gingivostomatitis herpetica, apthosis and herpes nasalis.

An "ointment" according to the present invention is a drug preparation for external use made of a base compound of spreadable material such as vaseline, to which are added the actual pharmaceutical active substances, such as D₂O, and/or non-pharmaceutical active substances, for example by mixing.

A "cream" in the sense of the present invention should be understood to mean an ointment according to the invention which can also contain other components, such as cosmetic active substances, e.g. perfumes, colorants and/or emulsifiers, e.g. lecithin. A distinction is generally made between a cream and a lotion, this distinction mostly being made depending on the viscosity level. According to the invention, a cream should also be understood to mean a lotion.

A "gel" in the sense of the present invention is the solution of a macromolecular substance, e.g. agarose, acrylic acid, alginic acid, polysiloxane or acrylamide, the concentration whereof is so high that under suitable conditions and if necessary with the addition of other substances (e.g. salts, acids, fillers, buffer substances) the dissolved macro-molecules bind into a sponge-like, three-dimensional skeleton in the cavities whereof there is a liquid. Hence gels have a relatively firm consistency. The viscosity lies between liquid and solid. Such a liquid is preferably pure D₂O or a mixture of D₂O and H₂O according to the invention.

A "hydrogel" in the sense of the invention describes a gel which is characterized by particularly high water uptake capacity, and in the sense of the invention it preferably consists of 20-99%, more preferably 70-99% and particularly preferably 80-99% of water, without however exhibiting the rheological properties of a classical liquid. In an especially preferred embodiment, the hydrogel is transparent-translucent and at the same time spreadable, without its morphology and integrity being affected by the spreading of the gel.

By way of example, the production of a formulation usable according to the invention, in particular of an ointment, cream or gel, is described in the examples. If such a formulation contains other pharmaceutical and/or non-pharmaceutical active substances, these are preferably added by mixing of the formulation. It can however be effected by any standard method known in the state of the art. Such methods and also the concentrations to be selected of the components or substances to be used are known to the person skilled in the art.

The concentrations of D₂O in a formulation usable according to the invention preferably lie in the following ranges:

for a cream or ointment, preferably in the range from 0.1 to 98 wt. %, preferably from 5 to 85 wt. %, also preferably from 10 to 80 wt. %, particularly preferably from 15 to 70 wt. %, more preferably from 20 to 60 wt. % and most preferably from 25 to 50 wt. % and for a gel preferably 0.1 to 99.8 wt. %, preferably from 10 to 99 wt. %, also preferably from 15 to 80 wt. %, particularly preferably from 20 to 70 wt. %, more preferably from 30 to 70 wt. % and most preferably from 35 to 65 wt. %.

The person skilled in the art will select the suitable concentration in particular depending on the indication in question, the state of the organism (patient) to be treated, the severity of the disease and the like.

In a particularly preferred embodiment, a formulation usable according to the invention also contains at least one inorganic or organic solvent. The solvent is preferably selected from the group consisting of ethanol, water and glycerol and mixtures thereof.

All the uses according to the invention disclosed in this specification are also applicable without restriction to a formulation according to the invention, unless the contrary is indicated. Likewise, uses and administrations of a combination according to the invention or a mixture of D₂O and H₂O according to the invention apply without restriction to a formulation according to the invention, unless the contrary is indicated.

The present invention is further explained on the basis of figures and the following examples, but these serve only for illustration and do not limit the subjects of the invention.

BRIEF DESCRIPTION OF THE FIGURES

FIG. 7 shows Table 1, which instead shows the number of viruses in a culture of the cell line A549 (human alveolar carcinoma basal epithelial cells), prepared according to Example 4, at the time 72 hours after infection for various viruses. The determination of the viral count was effected by electron microscopy by counting and taking the mean value for 20 non-lysed cells in the treated group and in the control group in each case; the protocols are described in Examples 6 to 17.

FIG. 8 shows Table 2, which instead shows the number of viruses in a modified culture of the cell line A549 (human alveolar carcinoma basal epithelial cells), prepared according to Example 5, at the time 72 hours after infection for various viruses. The determination of the viral count was effected by electron microscopy by counting and taking the mean value for 20 non-lysed cells in the treated group and in the control group in each case.

FIG. 9 shows Table 3, which instead shows the results for the efficacy of $D_2O$ hydrogel (treated) and $H_2O$ hydrogel (control) for the therapy of Aphtosis herpetica in man according to Example 20. The mean value of the "total symptom score" (TSS) was taken using the number of gel applications per aphta, and for "maximum size of the aphtha", "time between first symptoms and first gel application", "period until externally complete healing" and "period until freedom from pain" averaging was effected over the total number of aphthae treated per group (treated or control respectively) (i.e. including multiple incidences); the errors stated are the standard deviations.

FIG. 10 shows Table 4, which instead shows the results for the efficacy of $D_2O$ nasal spray (treated) and $H_2O$ nasal spray (control) for the prophylaxis of rhinovirus infections after infection with the rhinovirus strain HRV-39 (Example 21). The stated mean "total symptom score" (TSS) and viral RNA concentrations in the nasal "lavage" liquid were determined arithmetically from the values obtained per study day (total 5 values=5 days total duration of study); the errors stated are the standard deviation. For the study of the efficacy for prophylaxis, the first administration of the nasal spray was effected 6 hours before infection with the virus, and two further administrations were effected up to the time of infection.

FIG. 11 shows Table 5, which instead shows the results for the efficacy of $D_2O$ nasal spray (treated) and $H_2O$ nasal spray (control) for the therapy of rhinovirus infections after infection with the rhinovirus strain HRV-39 (Example 21). The stated mean "total symptom score" (TSS) and viral RNA concentrations in the nasal "lavage" liquid were determined arithmetically from the values obtained per study day (total 5 values=5 days total duration of study); the errors stated are the standard deviation. For the study of the efficacy for therapy, the first administration of the nasal spray was effected 2 hours after infection with the virus.

FIG. 12 shows Table 6, which instead shows the results for the efficacy of $D_2O$ aerosol (treated) and $H_2O$ aerosol (control) for the therapy of acute bronchitis as a result of an infection with human respiratory syncytial virus (HRSV) according to Example 22. The infection took place on day 0 of the study, the values for the HRSV RNA concentration and lung function diagnostic data (FEV2/FVC) were measured on days 1-7 of the study and are stated in the table as arithmetic mean values and the standard deviation thereof. The variation of both measured values with time is shown in FIGS. 5 and 6.

EXAMPLES

Example 1

Figure 1:
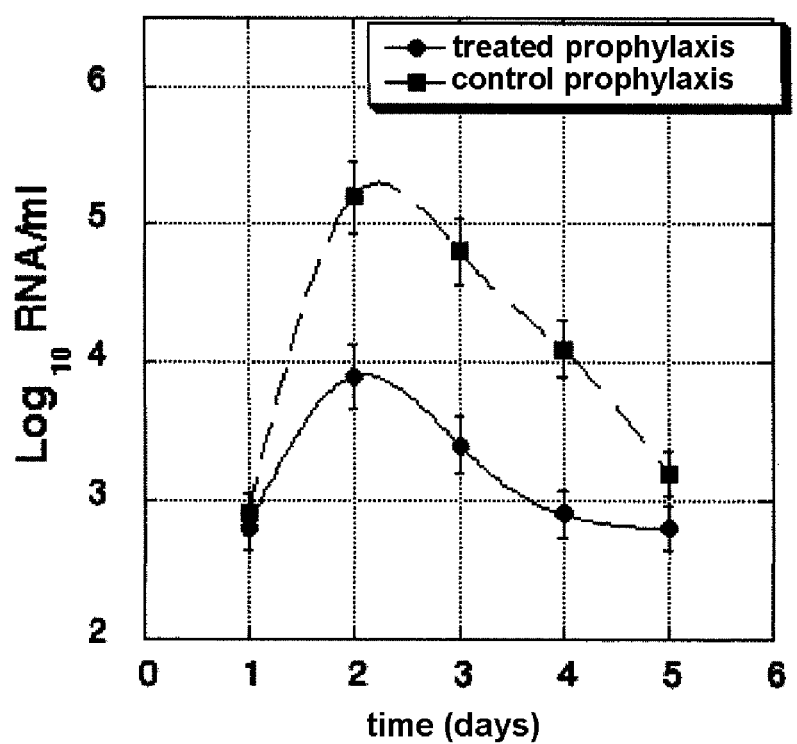
FIG. 1 shows the mean normalized concentration of HRV-39 RNA in the nasal "lavage" liquid of the prophylaxis group as a function of time after the HRV-39 infection (day 0) over the period of the study for the D₂O nasal spray (treated) and H₂O nasal spray (control) according to Example 21. In this group, the first administration of the nasal spray was given before infection with the virus.

Preparation of an Isotonic $D_2O$ or $H_2O$ Solution for Irrigation, Aerosolization or as Nasal Spray Deuterium oxide ($D_2O$) with an enrichment of 98% or purified water ($H_2O$) was mixed with 160 mM NaCl and adjusted to a pH value of 7.0 with 20 mM phosphate buffer (sodium dihydrogen phosphate and disodium hydrogen phosphate). The solutions were frozen at −70° C. and stored at −20° C. until use. For use as nasal spray, the solution was filled into standard ml pump spray bottles for nasal sprays and stored protected from light in the refrigerator until use.

Example 2

Preparation of a Hydrogel Based on Acrylic Acid

In separate preparations, 2.0 wt. % Carbopol 980 (manufacturer: Noveon Inc., 9911 Brecksville Rd., Cleveland Ohio 44141-3247, USA) was dissolved in pure $D_2O$ (98% D enrichment) or in pure $H_2O$ by stirring and then titrated to a pH value of 6.8 by pipetting with 10 M NaOH solution. Next, the colorless, transparent and optically clear acrylic acid gels (Carbopol gels) ($D_2O$ Carbopol gel and $H_2O$ Carbopol gel) formed by the NaOH addition as a result of cross-linking of the polyacrylic acid with the alkaline hydroxy groups via its carboxyl groups was stored at room temperature until further use, but for at least 24 hours.

Example 3

Preparation of an Aerosol

A PARI LC Plus Universal nebulizer (PARI GmbH, 82319 Starnberg, Germany) was used in combination with a Pari Universal compressor which created 200 mg/min of polydisperse aerosol with a mean particle size (mass median diameter) of 2.5-4.5 μm (operating pressure 2.0 bar, compressed air flow rate 6.0 l/min). The solutions prepared according to example were used for creating the aerosols. The particle size measurement was effected by dynamic light scattering in a flow-through cell. Aerosol creation was effected at a temperature of 30° C. with appropriate thermostatting of the nebulizer in a water-bath thermostat.

Example 4

Cell Culture Type 1

Cells of the cell line A549 (human alveolar carcinoma basal epithelial cells) from (American Type Culture Collection, Rockville, Md., USA) were seeded in 10 mm cell culture dishes at a cell density of $5\times10^4$ cells/cm². The medium used for this was Dulbecco's Modified Eagle Medium, DMEM (Gibco/BRL, Life Technologies Inc., Grand Island, N.Y., USA) with 10% fetal calf serum, FCS (Hyclone, Logan, Utah, USA), 100 U/ml penicillin and 100 μg/ml streptomycin (Sigma Chemical Co., St. Louis, Mo., USA). At a temperature of 37° C., the cells were grown to confluence at 95% atmospheric humidity and 5% $CO_2$. On the day of the infection of the cell culture with viruses, the cell culture medium was changed and the new medium (DMEM with 2% FCS and 100 U/ml penicillin and 100 μg/ml streptomycin) contained the viruses at a concentration which corresponded to a multiplicity of infection (MOI) of 3. At this MOI, the probability that a cell is infected with at least one viral particle was about 95%. The infection and incubation were effected under similar temperature and atmospheric humidity conditions to the aforesaid.

Example 5

Modified Cell Culture Type 1

Cells of the cell line A549 (human alveolar carcinoma basal epithelial cells) from (American Type Culture Collection, Rockville, Md., USA) were seeded in 10 mm cell culture dishes at a cell density of $5 \times 10^4$ cells/cm$^2$. The medium used for this was Dulbecco's Modified Eagle Medium, DMEM (Gibco/BRL, Life Technologies Inc., Grand Island, N.Y., USA) with 10% fetal calf serum, FCS (Hyclone, Logan, Utah, USA), 100 U/ml penicillin and 100 µg/ml streptomycin (Sigma Chemical Co., St. Louis, Mo., USA). At a temperature of 37° C., the cells were grown to confluence at 95% atmospheric humidity and 5% $CO_2$. After attainment of confluence and 24 hours before the infection of the cell culture with viruses, the cell culture medium was changed and the new medium (DMEM with 2% FCS and 100 U/ml penicillin and 100 µg/ml streptomycin) diluted with 30% $D_2O$, 98% enrichment (treated culture) or diluted with 30% $H_2O$ (control culture). At the time of infection, the medium was again exchanged for a medium of identical composition, which contained the viruses at concentrations which corresponded to a multiplicity of infection of 1. The infection and incubation were effected under similar temperature and atmospheric humidity conditions to the aforesaid.

Example 6

Determination of Viral Count After Incubation

After an incubation time of 3 days, the mean count of viruses per cell was investigated for the treated culture and the control culture. The viral counts were performed by transmission electron microscopy by standard fixing and staining methods (glutaraldehyde and osmium tetroxide). Before fixing, the cell culture medium was removed and the supernatant (after centrifugation at 20,000 g for 30 minutes) kept for further analyses. The viral particles contained in 20 randomly selected, non-lysed cells from the treated and from the control culture respectively were assessed by electron microscopy.

Example 7

Efficacy with Rhinoviruses 6 cell culture dishes of cell culture type 1 according to Example 4 were infected with rhinoviruses (strain RV-6 from American Type Culture Collection, Manassas, Va., USA). 120 minutes after the infection, the culture medium treated with the viruses was removed and replaced as follows by a diluted cell culture medium: in the treated group (3 culture dishes) by 30% $D_2O$ and 70% DMEM with 10% FCS and 100 U/ml penicillin and 100 µg/ml streptomycin. In the control group (3 culture dishes) instead of the $D_2O$, the same quantity of $H_2O$ was used for the dilution of the cell culture medium.

The determination of the viral count according to Example 7 for the treated and control cultures gave values which are shown in Table 1.

Example 8

Efficacy with Herpes Viruses Type 1 (Herpes Simplex Virus 1 (HSV-1))

6 cell culture dishes of cell culture type 1 according to Example 4 were infected with herpes viruses type 1, HSV-1 (strain MacIntyre VR-539, American Type Culture Collection, Manassas, Va., USA). 120 minutes after the infection, the culture medium treated with the viruses was removed and replaced as follows by a diluted cell culture medium: in the treated group (3 culture dishes) by 30% $D_2O$ and 70% DMEM with 10% FCS and 100 U/ml penicillin and 100 µg/ml streptomycin. In the control group (3 culture dishes) instead of the $D_2O$, the same quantity of $H_2O$ was used for the dilution of the cell culture medium.

The determination of the viral count according to Example 7 for the treated and control cultures gave values which are shown in Table 1.

Example 9

Efficacy with Herpes Viruses Type Varicella Zoster (Varicella Zoster Virus (VZV))

6 cell culture dishes of cell culture type 1 according to Example 4 were infected with herpes viruses of the type zoster, Varicella zoster, strain Ellen, VR-586 from American Type Culture Collection, Manassas, Va., USA). 120 minutes after the infection, the culture medium treated with the viruses was removed and replaced as follows by a diluted cell culture medium: in the treated group (3 culture dishes) by 30% $D_2O$ and 70% DMEM with 10% FCS and 100 U/ml penicillin and 100 µg/ml streptomycin. In the control group (3 culture dishes) instead of the $D_2O$, the same quantity of $H_2O$ was used for the dilution of the cell culture medium.

The determination of the viral count according to Example 7 for the treated and control cultures gave values which are shown in Table 1.

Example 10

Efficacy with Coronaviruses Type Human Coronavirus HCOV 229E 6 cell culture dishes of cell culture type 1 according to Example 4 were infected with human coronaviruses 229E. 120 minutes after the infection, the culture medium treated with the viruses was removed and replaced as follows by a diluted cell culture medium: in the treated group (3 culture dishes) by 30% $D_2O$ and 70% DMEM with 10% FCS and 100 U/ml penicillin and 100 µg/ml streptomycin. In the control group (3 culture dishes) instead of the $D_2O$, the same quantity of $H_2O$ was used for the dilution of the cell culture medium.

The determination of the viral count according to Example 7 for the treated and control cultures gave values which are shown in Table 1.

Example 11

Efficacy with Influenza Virus A 6 cell culture dishes of cell culture type 1 according to Example 4 were infected with influenza virus A, type H1N1. 120 minutes after the infection, the culture medium treated with the viruses was removed and replaced as follows by a diluted cell culture medium: in the treated group (3 culture dishes) by 30% D$_2$O and 70% DMEM with 10% FCS and 100 U/ml penicillin and 100 µg/ml streptomycin. In the control group (3 culture dishes) instead of the D$_2$O, the same quantity of H$_2$O was used for the dilution of the cell culture medium.

The determination of the viral count according to Example 7 for the treated and control cultures gave values which are shown in Table 1.

Example 12

Efficacy with Influenza Virus B 6 cell culture dishes of cell culture type 1 according to Example 4 were infected with influenza virus B/Hongkong/5/72. 120 minutes after the infection, the culture medium treated with the viruses was removed and replaced as follows by a diluted cell culture medium: in the treated group (3 culture dishes) by 30% D$_2$O and 70% DMEM with 10% FCS and 100 U/ml penicillin and 100 µg/ml streptomycin. In the control group (3 culture dishes) instead of the D$_2$O, the same quantity of H$_2$O was used for the dilution of the cell culture medium.

The determination of the viral count according to Example 7 for the treated and control cultures gave values which are shown in Table 1.

Example 13

Efficacy with Human Parainfluenza Virus 1

6 cell culture dishes of cell culture type 1 according to Example 4 were infected with human parainfluenza virus 1, strain Washington 1957 (HPIV-1). 120 minutes after the infection, the culture medium treated with the viruses was removed and replaced as follows by a diluted cell culture medium: in the treated group (3 culture dishes) by 30% D$_2$O and 70% DMEM with 10% FCS and 100 U/ml penicillin and 100 µg/ml streptomycin. In the control group (3 culture dishes) instead of the D$_2$O, the same quantity of H$_2$O was used for the dilution of the cell culture medium.

The determination of the viral count according to Example 7 for the treated and control cultures gave values which are shown in Table 1.

Example 14

Efficacy with Human Respiratory Syncytial Virus (HRSV)

6 cell culture dishes of cell culture type 1 according to Example 4 were infected with HSRV, strain Long. 120 minutes after the infection, the culture medium treated with the viruses was removed and replaced as follows by a diluted cell culture medium: in the treated group (3 culture dishes) by 30% D$_2$O and 70% DMEM with 10% FCS and 100 U/ml penicillin and 100 µg/ml streptomycin. In the control group (3 culture dishes) instead of the D$_2$O, the same quantity of H$_2$O was used for the dilution of the cell culture medium.

The determination of the viral count according to Example 7 for the treated and control cultures gave values which are shown in Table 1.

Example 15

Efficacy with Human Metapneumonia Virus A1 (HMPV)

6 cell culture dishes of cell culture type 1 according to Example 4 were infected with HMPV type A1. 120 minutes after the infection, the culture medium treated with the viruses was removed and replaced as follows by a diluted cell culture medium: in the treated group (3 culture dishes) by 30% D$_2$O and 70% DMEM with 10% FCS and 100 U/ml penicillin and 100 µg/ml streptomycin. In the control group (3 culture dishes) instead of the D$_2$O, the same quantity of H$_2$O was used for the dilution of the cell culture medium.

The determination of the viral count according to Example 7 for the treated and control cultures gave values which are shown in Table 1.

Example 16

Efficacy with Human Adenoviruses Type 3

6 cell culture dishes of cell culture type 1 according to Example 4 were infected with human adenoviruses type 3, strain GZ1. 120 minutes after the infection, the culture medium treated with the viruses was removed and replaced as follows by a diluted cell culture medium: in the treated group (3 culture dishes) by 30% D$_2$O and 70% DMEM with 10% FCS and 100 U/ml penicillin and 100 µg/ml streptomycin. In the control group (3 culture dishes) instead of the D$_2$O, the same quantity of H$_2$O was used for the dilution of the cell culture medium.

The determination of the viral count according to Example 7 for the treated and control cultures gave values which are shown in Table 1.

Example 17

Efficacy with Human Enteroviruses Type EV71

6 cell culture dishes of cell culture type 1 according to Example 4 were infected with human enteroviruses, type EV71, strain SHZH98. 120 minutes after the infection, the culture medium treated with the viruses was removed and replaced as follows by a diluted cell culture medium: in the treated group (3 culture dishes) by 30% D$_2$O and 70% DMEM with 10% FCS and 100 U/ml penicillin and 100 µg/ml streptomycin. In the control group (3 culture dishes) instead of the D$_2$O, the same quantity of H$_2$O was used for the dilution of the cell culture medium.

The determination of the viral count according to Example 7 for the treated and control cultures gave values which are shown in Table 1.

Example 18

Preventive Efficacy with Rhinoviruses 6 cell culture dishes of the modified cell culture type 1 according to Example 5 were infected with rhinoviruses (strain RV-16 from American Type Culture Collection, Manassas, Va., USA). 120 minutes after the infection, the culture medium treated with the viruses was removed and replaced as follows by a diluted cell culture medium: in the treated group (3 culture dishes) by 30% D$_2$O and 70% DMEM with 10% FCS and 100 U/ml penicillin and 100 µg/ml streptomycin. In the control group (3 culture dishes) instead of the D$_2$O, the same quantity of H$_2$O was used for the dilution of the cell culture medium.

The determination of the viral count according to Example 7 for the treated and control cultures gave values which are shown in Table 2.

Example 19

Preventive Efficacy with Herpes Viruses Type 2 (Herpes Simplex Virus 2 (HSV-2))

6 cell culture dishes of the modified cell culture type 1 according to Example 5 were infected with herpes viruses type 2, strain 734, from American Type Culture Collection, Manassas, Va., USA. 120 minutes after the infection, the culture medium treated with the viruses was removed and replaced as follows by a diluted cell culture medium: in the treated group (3 culture dishes) by 30% $D_2O$ and 70% DMEM with 10% FCS and 100 U/ml penicillin and 100 μg/ml streptomycin. In the control group (3 culture dishes) instead of the $D_2O$, the same quantity of $H_2O$ was used for the dilution of the cell culture medium.

The determination of the viral count according to Example 7 for the treated and control cultures gave values which are shown in Table 2.

Example 20

Efficacy for Therapy of Aphthosis Herpetica in Clinical Study 28 healthy volunteers aged from 20-45 years (14 female, 14 male) were selected for this study. All the test persons selected had a history of aphthosis herpetica in the region of the oral mucous membrane, particularly in the region of the lip mucous membrane, with at least 6 events per year.

None of the test persons used antiviral drugs or immuno-modulating drugs one week before or during the test which was limited to 3 months.

The 28 test persons were randomized into 2 groups (treated group and control group), each of 14 persons. Each test person received a 20 g tube of a hydrogel produced according to Example 2, the treated group a $D_2O$ hydrogel (prepared with 100% $D_2O$), and the control group a $H_2O$ hydrogel (prepared with 100% $H_2O$) with the instruction to apply this to the affected mucous membrane site immediately with the first symptoms of aphthosis herpetica and allow it to act for 1 minute. The application was to be repeated every 2 hours for the duration of 3 days during the waking hours. The test persons were directed to keep a record of administration (patient journal) and to note each application in this and also for each application the following symptom details (symptom scores), based on the previous application of the gel, on a scale from 1 (very little/small) to 5 (very marked/large): a) size of the aphtha, b) pain, c) depth. These 3 quantities were summed in the data assessment and the arithmetic mean value taken over the total number of the individual scores (=number of gel applications). Further, the maximum size reached by the aphtha treated, date and time the first symptoms were noticed, time of the start of therapy, time of the external complete healing of the aphtha, time of freedom from pain and the position of the aphtha were to be stated. For the data assessment, only aphthae which were situated in the mucous membrane region of the upper and lower lip were taken into account, since these regions could be well observed by pulling forward and their extent measured in front of the mirror by means of a measuring tape provided to the test persons. In these regions, the application of the gel was effected by 1) pulling the upper or lower lip forward, 2) application of gel to the site affected and 3) holding the lip pulled forward for 60 seconds in order to allow the permeation of the $D_2O(H_2O)$ into the mucous membrane. Further, all incidences of aphthae which were noted with first symptoms after 14.00 hrs on a given day were taken out of the assessment since in this case because of the sleep cycle an adequate treatment of the aphtha with hydrogel according to the stated medication plan was not guaranteed. The period of the study extended over 3 months. Altogether, assessable data was obtained in this way from 10 persons in the control group and 8 persons in the treated group; among these at least 2 incidences occurred during the study period in 6 persons in the control group and 5 persons in the treated group, and only one incidence in the remaining test persons. The results are presented in Table 3.

Example 21

Efficacy for the Prophylaxis and Therapy of Human Rhinovirus (HRV) Infections in Clinical Study As test persons, a total of 44 persons (25 male, 19 female) aged between 20-51 years were recruited on a voluntary basis. The selection criterion was an antibody titer of ≤1:2 with regard to the HRV strain which was used for infection. A further selection criterion was non-smoker, or the declared and credible willingness to stop smoking completely during the experiment and no manifestation of diseases of the respiratory tract for at least 2 weeks before entry into the study. Exclusion criteria were: a) asthma and other chronic diseases of the respiratory tract, b) disorders of taste or odor perception, c) use of nasal sprays or other nasal applications within 2 weeks before entry into the study, and d) pregnancy.

As the HRV strain for the infection of the test persons, the strain HRV 39 was used. For the purpose of the inoculation, the strain was administered to the test persons on day 0 in the study in the form of nasal drops with a virus concentration which corresponded to 200 times the 50% value of the infectious tissue culture concentration ($TCID_{50}$) and was dissolved in 200 μl of liquid (phosphate-buffered saline, pH 7.0). The administration of the infection virus HRV 39 as nasal drops was effected per test person (100 μl per nostril and administration) twice within 20 minutes in the lying position.

The total duration of the study was 5 days, calculated from the time of the HRV-39 infection. Directly before the infection, the test persons were divided randomly into 4 groups each of 11 persons: the treated groups A and B and the control groups C and D. The groups differed as regards the primary and secondary endpoints of the study. For the treated group A and the control group C (prophylaxis groups), the primary measure of efficacy was the reduction of the content of positive HRV-39 RNA, and the smallest possible change in the averaged "total symptoms score" (TSS) was the secondary measure of efficacy. For the treated group B and the control group D (therapy groups), the primary measure of efficacy was a reduction in the averaged TSS, which was made up of 6 individual symptoms. The secondary measure of efficacy in the therapy groups was the reduction in the content of positive HRV-39 RNA. In the therapy group, only test persons in whom a successful infection by inoculation with HRV-39 could be demonstrated were assessed. The criterion for this was an HRV-39 specific, serum-neutralized antibody titer elevated by at least a factor of 4.

During the 5 days of the study, nasal irrigation ("lavage" with 10 ml of phosphate-buffered saline per nostril) was performed in all test persons every 12 hours and the discharge obtained was frozen for subsequent RNA and viral titer analysis. Standard statistical methods were used for the comparison of the total symptoms scores of the therapy groups on the individual experiment days, in particular variance and covariance analyses.

The study medication was given single blind. The protocol was as follows: for the prophylaxis groups the administration of 200 µl per nostril of the nasal spray prepared according to Example 2 ($D_2O$ for treated group A and $H_2O$ for control group C) was effected every 2 hours during waking hours (at least 16 hrs per day). The administration was effected by 2 spray strokes of the pump sprayer for each nostril. 80-110 µl of liquid were released per spray stroke. The start of the medication was 4 hours before the infection with HRV-39, i.e. directly (ca. 5 mins) before the HRV-39 infection the prophylaxis groups received their third administration of the nasal spray. The end of the medication was the end of day 3 of the study. For the therapy groups, the first administration (same quantities as in the prophylaxis groups) of the nasal spray prepared according to Example 2 ($D_2O$ for treated group B and $H_2O$ for control group D) was effected 2 hours after the HRV-39 infection and then every 2 hours during the waking hours as defined above until the end of the fourth day of the study.

The "total symptom score" (TSS) used for the therapy- and treated group was made up of 6 individual scores (runny nose, sore throat, feeling ill, impairment of breathing through the nose, cough, sneezing), and each individual score could be assessed on a scale from 0 (very slight) to 5 (very high) by the test person, based on the previously experienced or felt maximum of the symptom in the previous assessment. The individual scores were taken twice daily (morning and evening) for each test person in the therapy groups. The 2 data sets obtained per day were then arithmetically averaged. The first symptom score was ascertained on day 0 directly before the HRV-39 infection.

The quantification of the HRV-39 RNA in the nasal lavage samples obtained was effected by standard methods by HRV-A TaqMan reverse transcription PCR assay. The determination of the serum-neutralizing antibody titer for HRV-39 from the nasal lavage samples was effected by standard methods.

Figure 2:
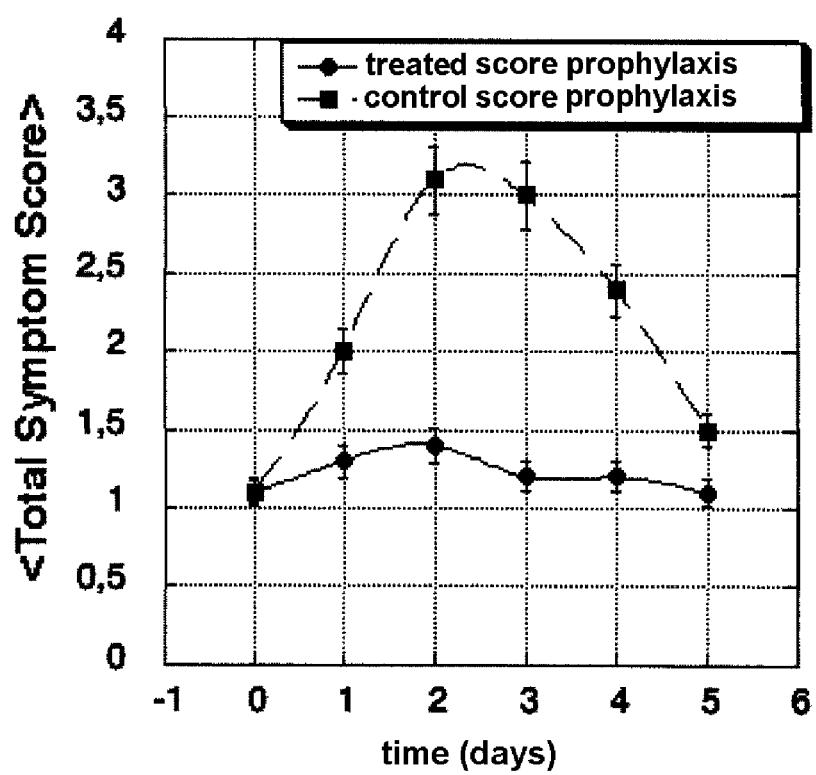
FIG. 2 shows the mean "total symptom score" (TSS) after HRV-39 infection (Example 21) of the prophylaxis group as a function of time after the HRV-39 infection (day 0) over the period of the study for the D₂O nasal spray (treated) and H₂O nasal spray (control). The TSS is made up of 6 individual symptoms which were each assessed on a scale from 1-5 and then summed. In this group, the first administration of the nasal spray was given before infection with the virus.
Figure 3:
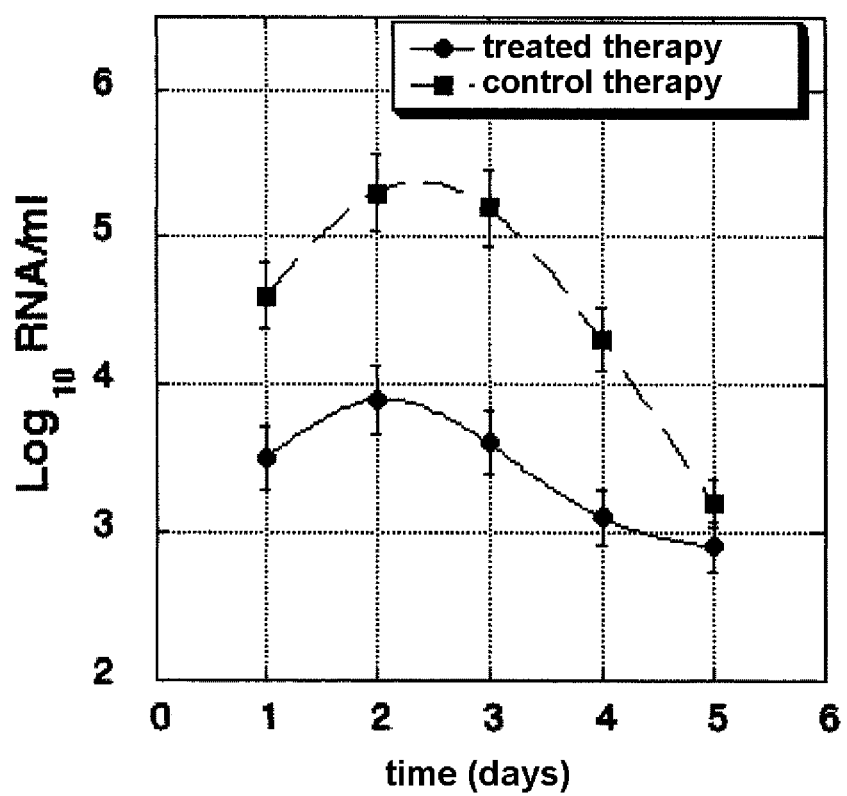
FIG. 3 shows the mean normalized concentration of HRV-39 RNA in the nasal "lavage" liquid of the therapy group as a function of time after the HRV-39 infection (day 0) over the period of the study for the D₂O nasal spray (treated) and H₂O nasal spray (control) according to Example 21. In this group, the first administration of the nasal spray was given 2 hours after infection with the virus.
Figure 4:
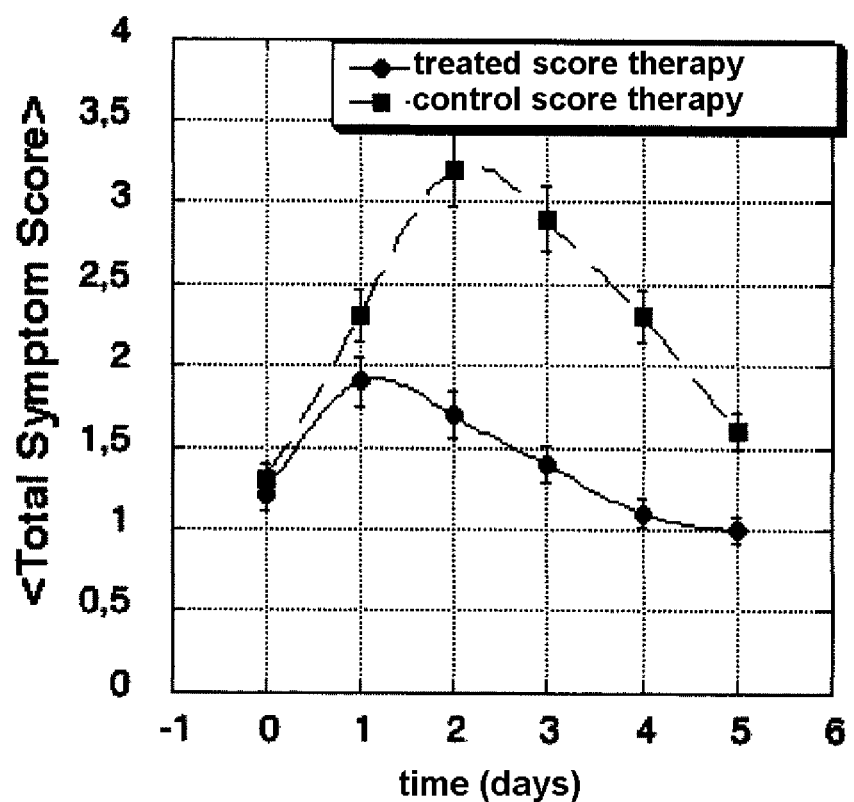
FIG. 4 shows the mean "total symptom score" (TSS) after HRV-39 infection (Example 21) of the therapy group as a function of time after the HRV-39 infection (day 0) over the period of the study for the D₂O nasal spray (treated) and H₂O nasal spray (control). The TSS is made up of 6 individual symptoms which were each assessed on a scale from 1-5 and then summed. In this group, the first administration of the nasal spray was given 2 hours after infection with the virus.

The results for the prophylaxis groups are shown in FIGS. 1 and 2 and in Table 4, and the results for the therapy groups are shown in FIGS. 3 and 4 and in Table 5.

Example 22

Efficacy for the Therapy of Infections with Human Respiratory Syncytial Virus (HRSV) in Clinical Study As test persons, a total of 18 persons (8 male, 10 female) aged between 20-44 years were recruited on a voluntary basis. The selection criterion was a history of hyperreactivity of the bronchial system to viral infections of the respiratory tract. A further selection criterion was non-smoker, or the declared and credible willingness to stop smoking completely during the experiment (duration 7 days) and no manifestation of diseases of the respiratory tract for at least 2 weeks before entry into the study. Exclusion criteria were: a) asthma and other chronic diseases of the respiratory tract, b) disorders of taste or odor perception and c) pregnancy.

As the HRSV strain for the infection of the test persons, the strain Long was used. For the purpose of the inoculation, the strain was administered to the test persons on day 0 of the study in the form of an aerosol with a virus concentration which corresponded to 200 times the 50% value of the infectious tissue culture concentration ($TCID_{50}$) and was dissolved in 200 µl of liquid (phosphate-buffered saline, pH 7.0). The administration of the HRSV was effected on day 0 of the study by two spray strokes with a hand atomizer into the pharyngeal space of the test person during inhalation. The time between the two spray strokes was 20 mins, and ca. 90-110 µl of liquid were atomized per spray stroke. Only those test persons in whom a dry cough occurred 24 hours at the latest after inoculation and in whom pneumonia could be excluded as the cause were admitted to the therapy.

The total duration of the study was 7 days, calculated from the time of the HRSV infection. Directly before the infection, the test persons were divided randomly into 2 groups each of 9 persons: treated group and control group. The primary endpoint of the study was defined from the predominant specificity of HRSV for infection of the lower respiratory tract and thus in particular the triggering of acute bronchitis. Associated with this is a measurable obstruction of the respiratory tract, which can be quantified with lung function diagnostic data (spirometer). As the baseline value, a spirometer measurement was performed directly before the HRSV infection. Accordingly, the primary purpose of the study was the lasting reduction of the spirometrically quantified respiratory tract obstruction as a consequence of the HRSV infection.

A secondary measure of efficacy was the reduction of the content of HRSV RNA in the liquid from a nasal "lavage", which was performed for the first time directly before the infection and then daily for the duration of the study. Only those test persons in whom a) a respiratory tract obstruction of at least 10% (based on the baseline value) could be measured and b) a successful infection by inoculation with HRSV could be demonstrated, were admitted for the assessment. The criterion for the latter was an HRSV specific antibody titer elevated by at least a factor of 4, determined by standard methods using ELISA.

During the 7 days of the study, a nasal rinsing ("lavage" with 10 ml of phosphate-buffered saline per nostril) was performed in all test persons every 24 hours and the discharge obtained was frozen for subsequent RNA and viral titer analysis.

The study medication was given single-blind. The protocol was as follows: for both groups the administration on each occasion of 10 ml of the isotonic NaCl solution prepared according to Example 2 in the form of an aerosol prepared according to Example 3 was effected 3 times daily. The administration of a single dose of the aerosol lasted 7 mins each time, i.e. 7 mins aerosol per test person 3 times daily. The first administration was effected 1 hour after the HRSV inoculation. The treated group received exclusively $D_2O$ and the control group exclusively $H_2O$ aerosol. The end of the medication was the evening of the $6^{th}$ study day.

The measurement of the obstruction of the lower respiratory tract was performed twice daily by means of a Vitalograph 2120 type spirometer according to the manufacturer's instructions (Vitalograph Ltd, Maids Moreton, Buckingham MK18 1SW, England) in the FVC ("forced vital capacity") mode, and the assessment was performed using the instrument's Spirotrac IV software. The quantities measured were the "forced vital volume" after 1-second exhalation (FEV1) and the "forced vital capacity" (FVC), and from these two quantities the ratio FEV1/FVC in percent was calculated and used as the characteristic quantity for the description of the obstruction of the respiratory tract caused by HRSV bronchitis.

The quantification of the HSRV RNA in the nasal lavage samples obtained on days 0-7 was effected by standard methods by reverse transcription PCR assay. The determination of the antibody titer for HRSV from the nasal lavage samples was effected by ELISA using an anti-HRSV antibody.

Figure 5:
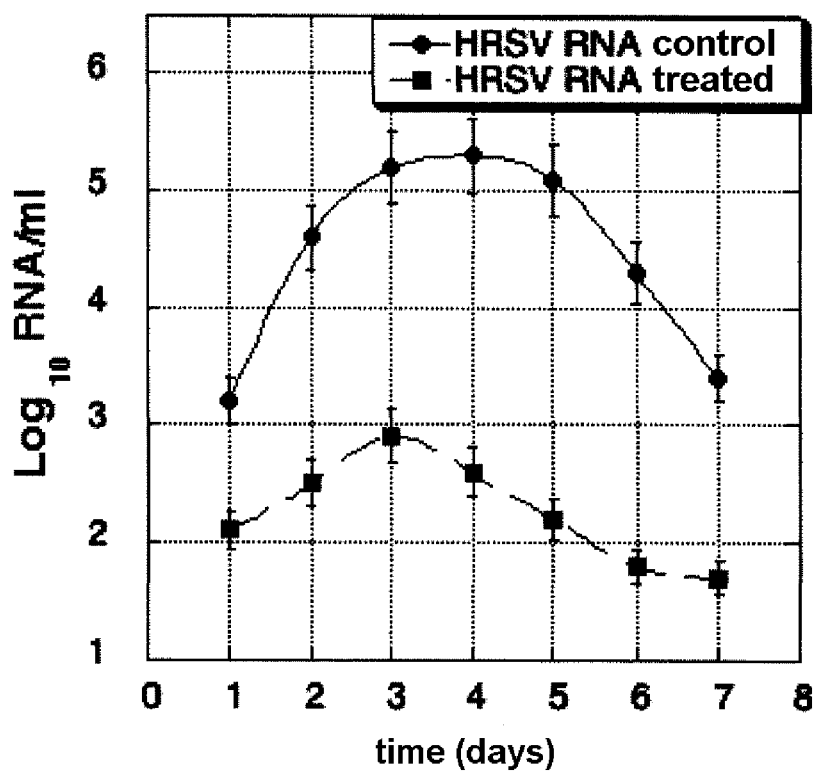
FIG. 5 shows the mean normalized concentration of HRSV RNA in the nasal "lavage" liquid from treated and control group as a function of time after the HRSV infection (day 0) over the period of the study for D₂O aerosol (treated) and H₂O aerosol (control) according to Example 22.
Figure 6:
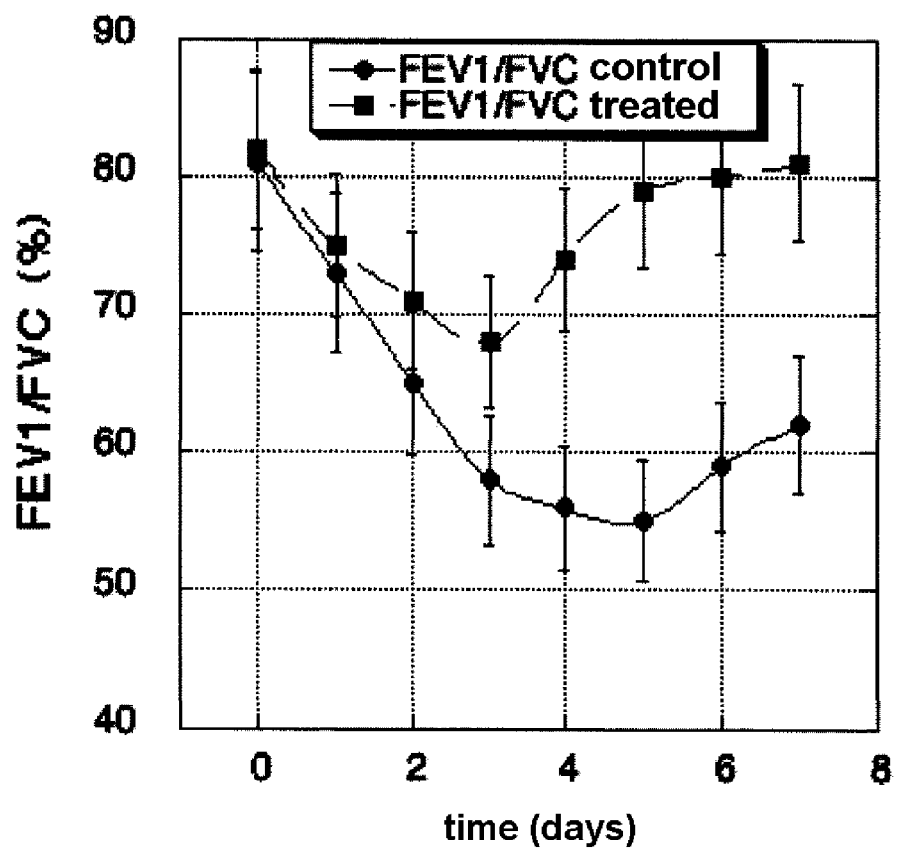
FIG. 6 shows the lung function diagnostic data after an HRSV infection according to Example 22 over the period of the study (7 days, infection on day 0). The "forced vital volume" after 1-second exhalation (FEV1) is shown, normalized to the "forced vital capacity" (FVC) in percent (FEV1/FVC×100) as a function of the study duration. The treated group received 3 doses of the $D_2O$ aerosol daily, and the control group received equal administrations of the $H_2O$ aerosol.

The results are shown in FIGS. 5 and 6 and in Table 6.

Example 23

Preparation of a D$_2$O-Containing Cream

D$_2$O was added slowly to 50 grams of Asche base cream (manufacturer: Asche Chiesi GmbH, Hamburg, Germany) with constant stirring at 40° C., until a weight content of 38% D$_2$O (based on the starting weight of the cream) in the homogenous mixture was reached. The cream was then cooled to room temperature and stored hermetically sealed.

The invention claimed is:

1. A method for treating a virus-based disease of the respiratory tract wherein said method comprises administering to the respiratory tract of a subject in need of such treating an amount effective of deuterium oxide to treat the virus-based disease, wherein the disease is selected from the group consisting of acute rhinitis, chronic rhinitis, rhinitis sicca, pharyngitis, tracheitis, acute bronchiolitis, chronic bronchiolitis, acute bronchitis, chronic bronchitis, pneumonia, acute sinusitis, and chronic sinusitis.

2. The method, according to claim 1, used to treat a combination of two or more of the virus-based diseases of the respiratory tract.

3. The method, according to claim 2, wherein the two or more virus-based diseases of the respiratory tract occur simultaneously or successively.

4. The method, according to claim 1, wherein the virus is of a family selected from the group consisting of Picornaviridae and, Paramyxoviridae.

5. The method, according to claim 1, wherein the virus is a virus of a genus selected from the group consisting of Rhinovirus, and Pneumovirus.

6. The method, according to claim 1, wherein the virus is a virus of a species selected from the group consisting of rhinovirus and respiratory syncytial virus (RSV).

7. The method, according to claim 1, wherein the deuterium oxide hydrates the respiratory tract.

8. The method, according to claim 1, wherein the deuterium oxide is used in combination with at least one other pharmaceutically active substance and/or at least one other non-pharmaceutically active substance.

9. The method, according to claim 8, wherein the at least one other pharmaceutically active substance is selected from the group consisting of viro-static agents, sympathomimetic agents, proteins, peptides, nucleic acids and immunosuppressant substances.

10. The method, according to claim 8, wherein the at least one other non-pharmaceutically active substance is selected from the group consisting of pharmaceutically compatible inorganic or organic acids or bases, polymers, copolymers, block copolymers, monosaccharides, polysaccharides, ionic and nonionic surfactants and lipids and mixtures thereof, albumin, transferrin and DNA repair proteins.

11. The method, according to claim 1, wherein the deuterium oxide is administered as an aerosol.

12. The method, according to claim 1, wherein the deuterium oxide is administered as a formulation.

13. The method, according to claim 12, wherein the formulation is a vapor or liquid.

14. The method of claim 1, wherein the subject is a human subject.

15. The method of claim 1, wherein the disease is selected from the group consisting of acute rhinitis, acute bronchiolitis, and acute bronchitis.

16. The method of claim 15, wherein the subject is a human subject.

17. The method of claim 1, where the deuterium oxide is the only pharmaceutically active substance administered to the subject for treating the virus-based disorder of the respiratory tract.

18. The method of claim 1, wherein the disease is acute bronchitis.

19. The method of claim 14, wherein the disease is acute bronchitis.

20. The method of claim 1, wherein the disease is acute rhinitis.

21. The method of claim 14, wherein the disease is acute rhinitis.

* * * * *